(12) United States Patent
Pepin et al.

(10) Patent No.: US 9,962,115 B2
(45) Date of Patent: May 8, 2018

(54) EYE-MOUNTABLE DEVICES AND STRUCTURES FOR EYE-MOUNTABLE DEVICES

(71) Applicant: Verily Life Sciences LLC, Mountain View, CA (US)

(72) Inventors: Brian Marc Pepin, Oakland, CA (US); James Etzkorn, Mountain View, CA (US); Mandy Philippine, Oakland, CA (US); Stephen O'Driscoll, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days. days.

(21) Appl. No.: 15/608,808

(22) Filed: May 30, 2017

(65) Prior Publication Data

US 2017/0258380 A1    Sep. 14, 2017

Related U.S. Application Data

(63) Continuation of application No. 14/696,367, filed on Apr. 24, 2015, now Pat. No. 9,681,829.

(51) Int. Cl.
*A61B 5/00*         (2006.01)
*A61B 5/145*        (2006.01)
(Continued)

(52) U.S. Cl.
CPC ........ *A61B 5/14532* (2013.01); *A61B 5/1477* (2013.01); *A61B 5/6821* (2013.01); *A61B 2560/0214* (2013.01); *G02C 7/04* (2013.01)

(58) Field of Classification Search
CPC ... A61B 5/1468; A61B 5/1477; A61B 5/6821; A61B 5/14532
See application file for complete search history.

(56) References Cited

U.S. PATENT DOCUMENTS 8,721,074 B2    5/2014  Pugh et al.
2010/0076553 A1  3/2010  Pugh et al.
(Continued)

OTHER PUBLICATIONS

International Search Report and Written Opinion prepared by the European Patent Office in international patent application serial No. PCT/1JS2016/027463 dated Jul. 15, 2016.
(Continued)

*Primary Examiner* — Christian Jang
(74) *Attorney, Agent, or Firm* — McDonnell Boehnen Hulbert & Berghoff LLP

(57) ABSTRACT

An eye-mountable device includes a transparent polymer and a structure embedded in the transparent polymer. The transparent polymer defines a posterior side and an anterior side of the eye-mountable device, and the transparent polymer has a concave surface and a convex surface. The structure includes a substrate, an antenna comprising a conductive loop, and a sensor that is configured to detect an analyte. The substrate includes a loop portion and a tab portion, where the loop portion has an outer circumference defined by an outer diameter and an inner circumference defined by an inner diameter, and where the tab portion extends from the inner circumference of the loop portion towards a center of the loop portion. The conductive loop is disposed on the loop portion of the substrate between the inner circumference and outer circumference, and the sensor is disposed on the tab portion of the substrate.

20 Claims, 9 Drawing Sheets

(51) Int. Cl.
*A61B 5/1477* (2006.01)
*G02C 7/04* (2006.01)

(56) References Cited

U.S. PATENT DOCUMENTS

| | | |
|---|---|---|
| 2012/0238857 A1 | 9/2012 | Wong et al. |
| 2012/0245444 A1 | 9/2012 | Otis et al. |
| 2012/0259188 A1 | 10/2012 | Besling |
| 2014/0350372 A1 | 11/2014 | Pugh et al. |
| 2014/0371558 A1 | 12/2014 | Etzkorn et al. |
| 2015/0005602 A1 | 1/2015 | Lindhardt |
| 2015/0061990 A1 | 3/2015 | Toner et al. |

OTHER PUBLICATIONS

Happich, "Medical contact lens embedds wireless MEMs sensor", Mar. 25, 2010; http:/fwww.electronics- eetimes.com/en/medical-contact-lens-embedds-wireless-mems-sensor.html?cmp_id=7&news_id=222901145.

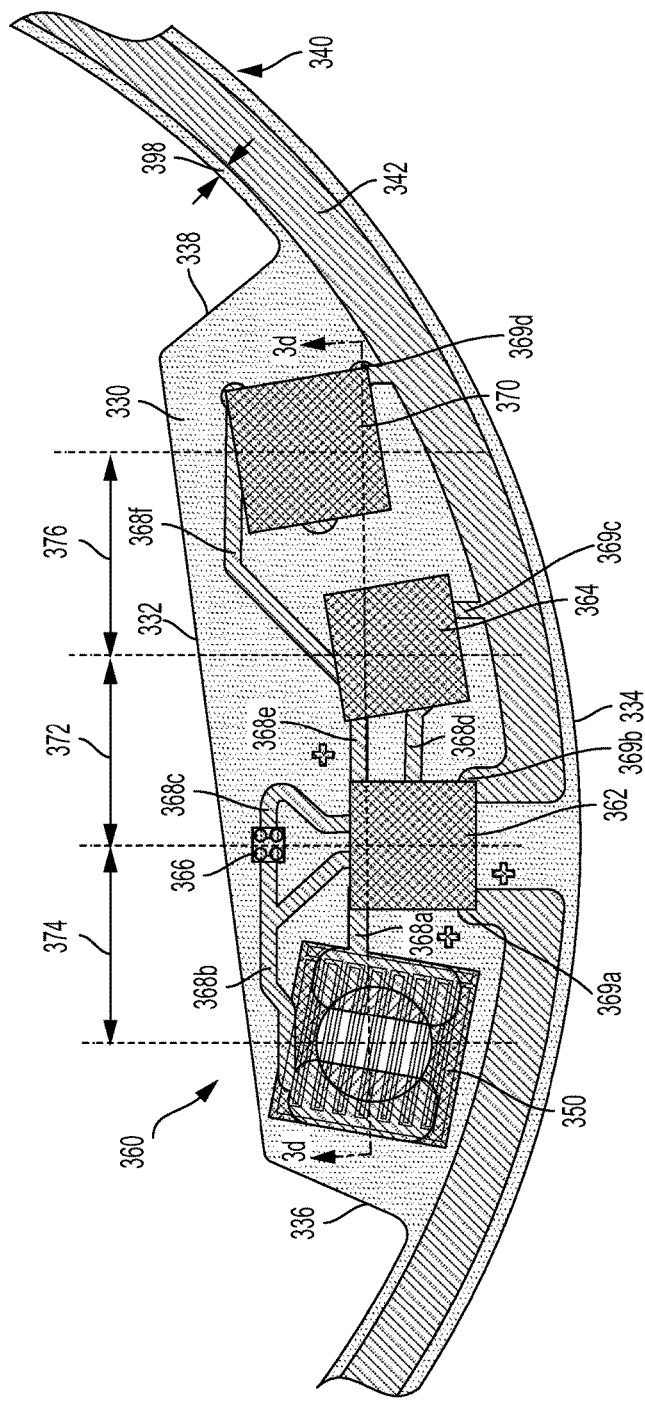
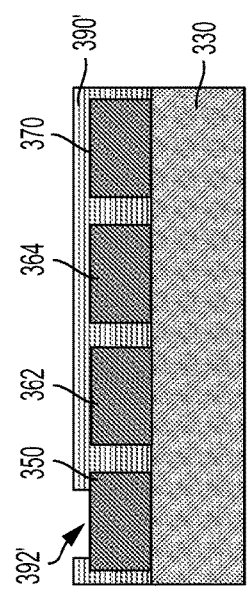
FIG. 3c
FIG. 3d

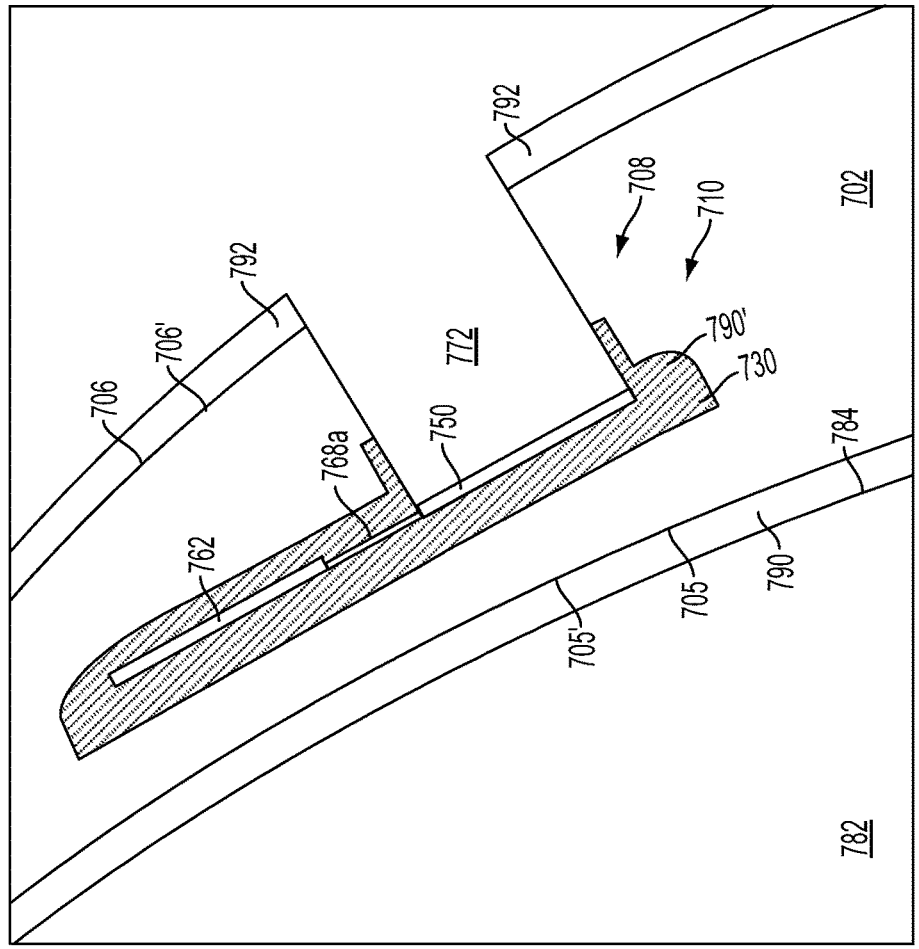
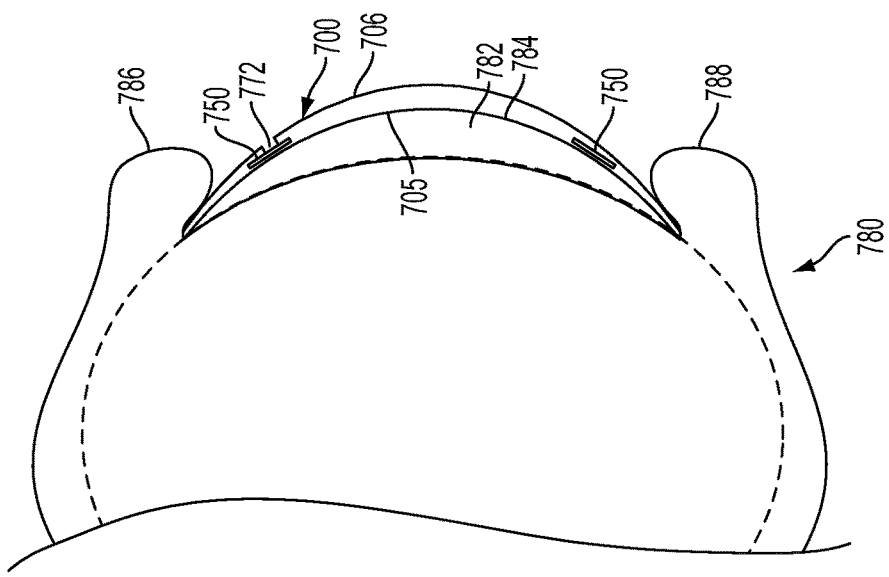
FIG. 7b
FIG. 7a

EYE-MOUNTABLE DEVICES AND STRUCTURES FOR EYE-MOUNTABLE DEVICES

CROSS-REFERENCE TO RELATED APPLICATION

This application is a continuation of application Ser. No. 14/696,367, filed Apr. 24, 2015, which is incorporated herein by reference.

BACKGROUND

Unless otherwise indicated herein, the materials described in this section are not prior art to the claims in this application and are not admitted to be prior art by inclusion in this section.

A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose) in a tear film of a user wearing the eye-mountable device. The body-mountable device may also be configured to monitor various other types of health-related information.

SUMMARY

In one aspect, an eye-mountable device is disclosed. An example body-mountable device includes: a transparent polymer, wherein the transparent polymer defines a posterior side and an anterior side of the eye-mountable device, and wherein the transparent polymer has a concave surface and a convex surface, and wherein the concave surface is configured to be removably mounted over a corneal surface and the convex surface is configured to be compatible with eyelid motion when the concave surface is so mounted; and a structure embedded in the transparent polymer, wherein the structure comprises: a substrate comprising a loop portion and a tab portion, wherein the loop portion has an outer circumference defined by an outer diameter and an inner circumference defined by an inner diameter, and wherein the tab portion extends from the inner circumference of the loop portion towards a center of the loop portion, an antenna comprising a conductive loop, wherein the conductive loop is disposed on the loop portion of the substrate between the inner circumference and the outer circumference, and a sensor disposed on the tab portion of the substrate, wherein the sensor is configured to detect an analyte.

In another aspect, a structure configured to be embedded in a transparent polymer is disclosed. An example structure includes: a substrate comprising a loop portion and a tab portion, wherein the loop portion has an outer circumference defined by an outer diameter and an inner circumference defined by an inner diameter, wherein the tab portion extends from the inner circumference of the loop portion towards a center of the loop portion, and wherein the tab portion of the substrate comprises: an outer edge corresponding to the outer circumference of the loop portion, an inner edge opposite the outer edge, and first and second side edges that extend inwardly from the inner circumference of the loop portion of the substrate to the inner edge of the tab portion of the substrate, wherein the first and second side edges of the tab portion of the substrate are substantially perpendicular to the inner circumference of the loop portion of the substrate; an antenna comprising a conductive loop, wherein the conductive loop is disposed on the loop portion of the substrate between the inner circumference and the outer circumference; and a sensor disposed on the tab portion of the substrate, wherein the sensor is configured to detect an analyte, wherein the transparent polymer defines a posterior side and an anterior side of an eye-mountable device, wherein the transparent polymer has a concave surface and a convex surface, and wherein the concave surface is configured to be removably mounted over a corneal surface and the convex surface is configured to be compatible with eyelid motion when the concave surface is so mounted.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3c is a partial top view of the structure shown in FIG. 3a, according to an example embodiment.

FIG. 3d is a partial side cross-section view of the structure shown in FIG. 3c, according to an example embodiment.

FIG. 7a is a side cross-section view of an eye-mountable device while mounted over a corneal surface of an eye, according to an example embodiment.

FIG. 7b is a side cross-section view showing tear film layers surrounding the surfaces of the eye-mountable device mounted as shown in FIG. 7a, according to an example embodiment.

DETAILED DESCRIPTION

Figure 1:
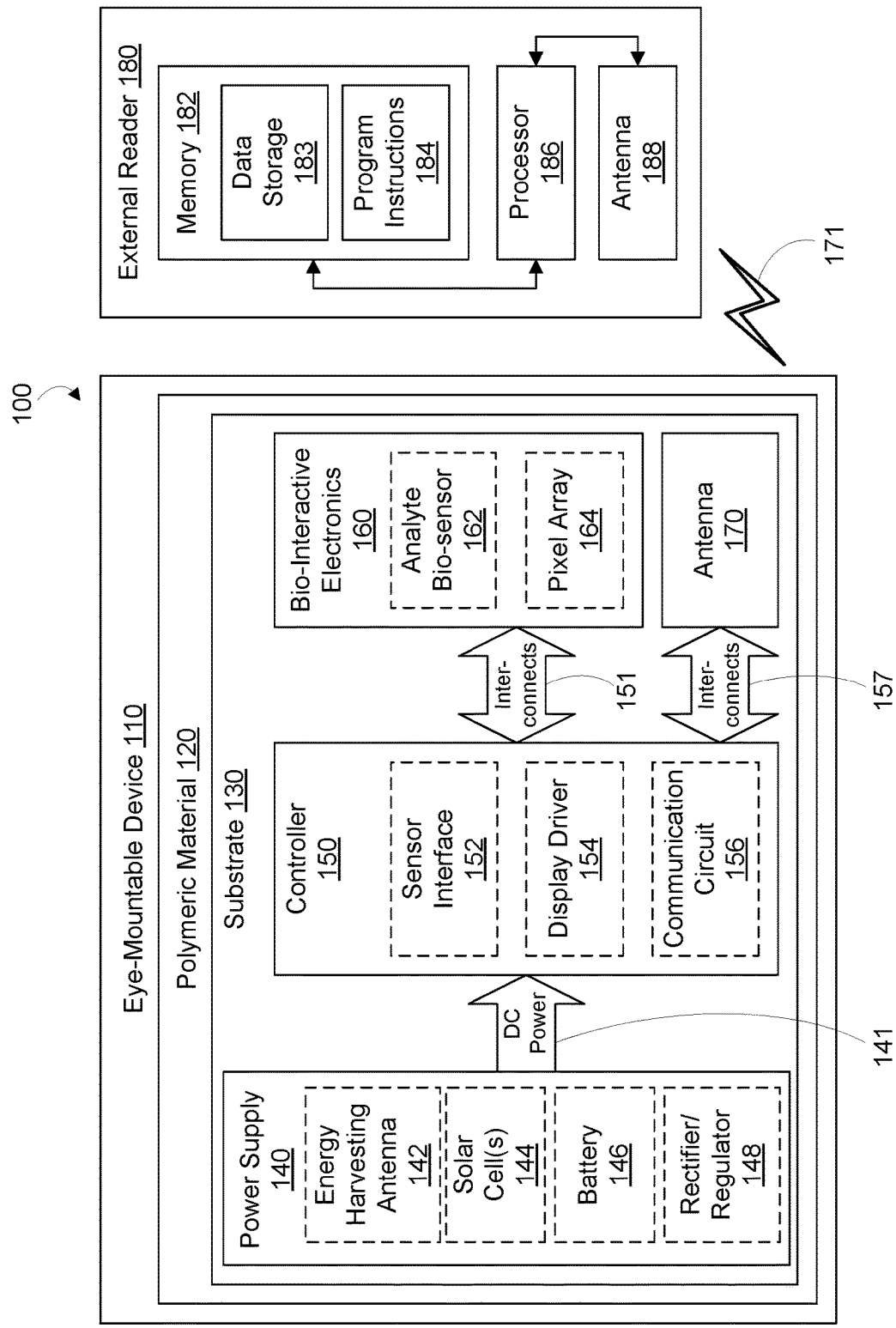
FIG. 1 is a block diagram of a system that includes an eye-mountable device in wireless communication with an external reader, according to an example embodiment.

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. Introduction

An eye-mountable device may include a transparent polymer and a structure embedded in the transparent polymer.

The transparent polymer may define a posterior side and an anterior side of the eye-mountable device, and the transparent polymer may have a concave surface and a convex surface. The concave surface may be configured to be removably mounted over a corneal surface and the convex surface may be configured to be compatible with eyelid motion when the concave surface is so mounted. Moreover, the structure may include substrate, an antenna that includes a conductive loop, and a sensor that may be configured to detect an analyte. The conductive loop and the sensor may be disposed on the substrate.

A variety of parameters of the structure may affect comfort of a wearer of the eye-mountable device and/or power delivery of the antenna. For example, one or more dimensions of the substrate, conductive loop, and/or sensor may affect the comfort of the wearer of the eye-mountable device and/or power delivery of the antenna. As another example, the location of the conductive loop and/or sensor on the substrate may affect the comfort of the wearer of the eye-mountable device and/or power delivery of the antenna.

In an example embodiment, the substrate may include a loop portion and a tab portion, where the loop portion may have an outer circumference defined by an outer diameter and inner circumference defined by an inner diameter, and where the tab portion may extend from the inner circumference of the loop portion towards the center of the loop portion. With this arrangement, the conductive loop of the antenna may be disposed on the loop portion of the substrate and the sensor may be disposed on the tab portion of the substrate. Beneficially, structures described herein may improve comfort of the wearer of the eye-mountable device (e.g., reduce differential pressure transmitted from the transparent polymer to the wearer) and power delivery of the antenna.

As used throughout this disclosure, the anterior side of the eye-mountable device refers to an outward-facing side of the eye-mountable device, whereas the posterior side of the eye-mountable device refers to an inward-facing side of the eye-mountable device. In particular, when the eye-mountable device is mounted on an eye of the user, the anterior side corresponds to a side of the eye-mountable device that is facing outward and thus not touching the eye of the user. Further, when the eye-mountable device is mounted on an eye of the user, the posterior side corresponds to a side of the eye-mountable device that is facing inward and thus touching the eye of the user.

II. Example Systems

An eye-mountable device may be configured to monitor health-related information based on at least one analyte detected in a fluid of a user wearing the eye-mountable device. An example eye-mountable device that is configured to detect the at least one analyte in a tear film of a user wearing the eye-mountable device will now be described in greater detail.

A structure in accordance with an exemplary embodiment may include a sensor, electronics, and an antenna. The electronics may operate the sensor to perform readings and operate the antenna to wirelessly communicate the readings from the sensor to an external reader via the antenna. The sensor can be arranged on the substrate to face outward, away from the corneal surface of the user, so as to generate clinically relevant readings from tear fluid of the user that the sensor receives via a channel in the anterior side of the eye-mountable device. For example, the sensor can be suspended in the lens material and situated such that the sensor is less than 10 micrometers from the anterior side of the eye-mountable device. The sensor can generate an output signal indicative of a concentration of an analyte that the sensor receives via the channel. In addition, in some embodiments, the structure may further include a battery situated on the substrate. The battery may be configured to provide electrical power to the electronics.

FIG. 1 is a block diagram of a system 100 with an eye-mountable device 110 in wireless communication with an external reader 180, according to an example embodiment. The exposed regions of the eye-mountable device 110 are made of a polymeric material 120 formed to be contact-mounted over a corneal surface of an eye. In some embodiments, the polymeric material 120 may comprise one or more polymer layers.

Substrate 130 is embedded in the polymeric material 120 to provide a mounting surface for a power supply 140, a controller 150, bio-interactive electronics 160, and an antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it may also be referred to as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material 120 due to the concave curvature. While mounted with the concave surface against the eye, the anterior or outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of resists, masks, and deposition techniques can be employed to pattern materials on the substrate 130.

The substrate 130 can be a relatively rigid polymeric material, such as PET, paralyene or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in the center region of the eye-mountable device 110. The bio-interactive electronics 160 and/or the substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display driver instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the anterior side of the eye-mountable device 110.

The power supply 140 is configured to power the controller 150 and bio-interactive electronics 160. For example, a radio-frequency energy harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the antenna 170 and the energy harvesting antenna 142 can be accomplished with the same physical antenna.

In addition, the power supply 140 may include a battery 146. The battery 146 may comprise a solid-state device. In some examples, the battery 146 may be a re-chargeable battery. In other examples, the battery 146 may be a single-use battery. In some examples, the battery 146 may be connected to the controller 150 and/or the antenna 170 via interconnects (not shown in FIG. 1).

A rectifier/regulator 148 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 148. The rectifier/regulator 148 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 148 can include one or more energy storage devices arranged to mitigate high frequency variations in the ambient energy harvesting antenna 142 and/or solar cell(s) 144. For example, an energy storage device (e.g., capacitor, inductor, etc.) can be connected to the output of the rectifier/regulator 148 so as to function as a low-pass filter. In addition, the rectifier/regulator 148 could provide a DC supply voltage 141 from the battery 146. In some embodiments, the rectifier/regulator 148 could generate a voltage used to recharge the battery 146. With this arrangement, captured energy from the energy-harvesting antenna 142, solar cell(s), and/or the inertial power scavenging system may be used to recharge the battery 146.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such as an analyte bio-sensor 162, in bio-interactive electronics 160 to obtain input from the biological environment. Alternatively or additionally, the interaction could involve the use of one or more components, such as the pixel array 164, to provide an output to the biological environment.

In one example, a sensor interface module 152 can be included for operating the analyte bio-sensor 162. The analyte bio-sensor 162 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 152 can be a potentiostat configured to apply a voltage difference between the working and reference electrodes while measuring a current through the working electrode.

In some instances, a reagent can also be included to sensitize the electrochemical sensor to desired analytes. For example, a layer of glucose oxidase ("GOX") can be situated around the working electrode to catalyze glucose into hydrogen peroxide ($H_2O_2$). The hydrogen peroxide can then be oxidized at the working electrode, which releases electrons to the working electrode, which generates a current.

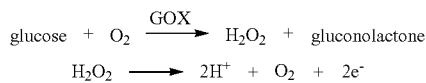

$$H_2O_2 \longrightarrow 2H^+ + O_2 + 2e^-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

The controller 150 can optionally include a display driver module 154 for operating the pixel array 164. The pixel array 164 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye. In some embodiments, the battery 146 may be configured to provide electrical power to the pixel array 164.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the external reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 148 is illustrated in the power supply block 140, the rectifier/regulator 148 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components of the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the antenna 170 can be implemented with the same physical antenna. For example, a loop antenna can both harvest incident radiation for power generation and communicate information via backscatter radiation.

The external reader 180 includes an antenna 188 (or group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g., RAM) or non-volatile (e.g., ROM) storage system readable by the processor 186. The memory 182 can include a data storage 183 to store indications of data structures, such as sensor readings (e.g., from the analyte bio-sensor 162), program settings (e.g., to adjust behavior of the eye-mountable device 110 and/or external reader 180), etc. The memory can also include program instructions 184 for execution by the processor 186 to cause the external reader to perform processes specified by the program instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged into a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in eyeglasses, integrated in a piece of jewelry such as a necklace, earring, etc., or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the antenna 170) are rectified and/or regulated in the rectifier/regulator 148 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162 sufficient to cause the analyte to undergo an electrochemical reaction at the working electrode. The current through the working electrode can be measured to provide the sensor output indicative of the analyte concentration. The controller 150 can operate the antenna 170 to communicate the sensor results back to the external reader 180 (e.g., via the communication circuit 156). The sensor result can be communicated by, for example, modulating an impedance of the antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the on-board controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

In addition, the radio frequency radiation 171 may be supplied to charge the battery 146. In some examples, the supplied radio frequency radiation 171 can charge the battery 146 long enough so that the battery 146 is fully charged. Further, in some examples, the supplied radio frequency radiation 171 can charge so that the battery 146 is less than fully charged.

Further, in some embodiments, the battery 146 may provide power to the controller 150 to operate the analyte bio-sensor 162 to measure an analyte concentration level. And in at least one such embodiment, the battery 146 may reduce or eliminate the need for continuous radio frequency radiation 171 from the external reader 180. With this arrangement, the battery 146 may permit autonomous operation of the eye-mountable device 110. For example, the battery 146 may bias the analyte bio-sensor 162, via a potentiostat, so that electrodes in the analyte bio-sensor 162 are at appropriate potentials for analyte measurement. As another example, the battery 146 may power a memory in the controller 150, for data logging of sensor readings from analyte bio-sensor 162.

III. Example Substrates

Figure 2:
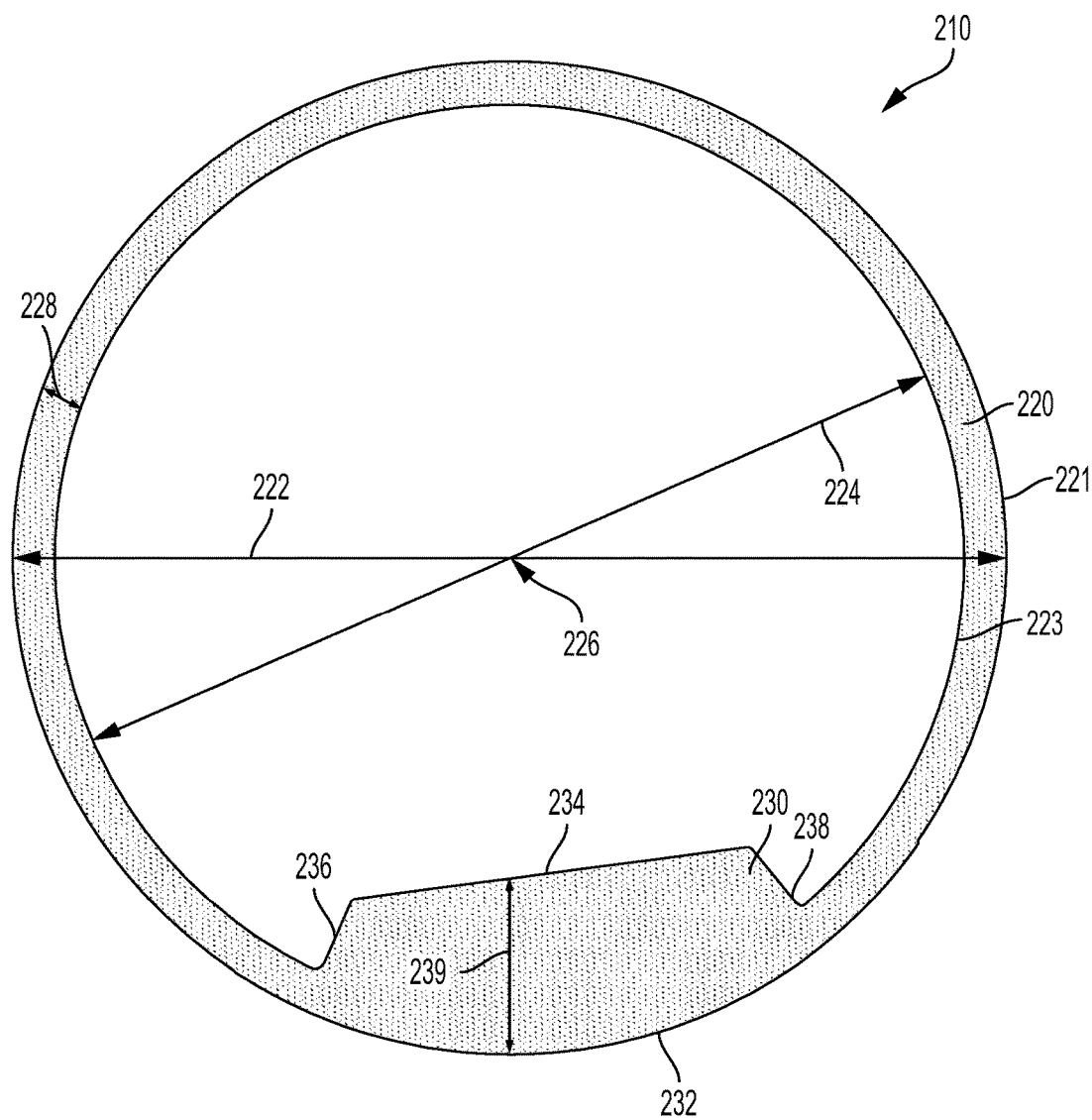
FIG. 2 is a top view of a substrate, according to an example embodiment.

FIG. 2 is a top view of a substrate 210, according to an example embodiment. The substrate 130 may take the form of or be similar to the substrate 210. It is noted that the relative dimensions in FIG. 2 and other Figures in this disclosure are not necessarily to scale, but have been rendered for purposes of explanation only in describing the arrangement of substrates, structures, and eye-mountable devices described herein.

The substrate 210 may include a loop portion 220 and a tab portion 230. The loop portion 220 of the substrate 210 may have an outer circumference 221 defined by an outer diameter 222 and an inner circumference 223 defined by an inner diameter 224. Moreover, the loop portion 220 may have a center 226.

The loop portion 220 of the substrate 210 may have a variety of dimensions. For instance, in some embodiments, the outer diameter 222 of the loop portion 220 may be between about 9.70 millimeters and 11.90 millimeters, such as 10.84 millimeters. Moreover, in some embodiments, the inner diameter 224 of the loop portion 220 may be between 9.50 micrometers and 11.50 micrometers, such as 10.46 micrometers. Further, in some embodiments, the outer diameter 222 of the loop portion 220 and/or the inner diameter 224 of the loop portion 220 may be selected to be less than a portion of the eye of a wearer of an eye-mountable device, such as the limbus of the eye of the wearer of the eye-mountable device. Further still, the loop portion 220 may have a width dimension 228 between 275 micrometers and 600 micrometers, such as 450 micrometers. In addition, the loop portion 220 may have a variety of thicknesses. For instance, in some embodiments, the loop portion 220 may have a thickness of about 25 micrometers. Moreover, in some embodiments, the loop portion 220 may have a thickness of about 27 micrometers.

Moreover, the loop portion 220 of the substrate 210 may comprise a variety of materials. For instance, in some embodiments, the loop portion 220 may comprise paralyene, PET, silicone (e.g., spray coated silicone), and cyclical olefin copolymers.

The tab portion 230 of the substrate 210 may extend from the inner circumference 223 of the loop portion 220 towards the center 226 of the loop portion 220. Moreover, the tab portion 230 of the substrate 210 may include an outer edge 232 corresponding to the outer circumference 221 of the loop portion 220, an inner edge 234 opposite the outer edge 232, and a first side edge 236 and a second side edge 238 that each extend inwardly from the inner circumference 223 of the loop portion 220 to the inner edge 234 of the tab portion 230. Further, in some embodiments, the first side 236 and the second side 238 of the tab portion 230 may be substantially perpendicular to the inner circumference 223 of the loop portion 220. The term "substantially perpendicular," as used in this disclosure, refers to exactly perpendicular and/or one or more deviations from exactly perpendicular that do not significantly impact comfort of a wearer of an eye-mountable device and power delivery of an antenna of the eye-mountable device as described herein.

The tab portion 230 of the substrate may have a variety of dimensions. For instance, in some embodiments, the tab portion 230 may have a width dimension 239 between the inner edge 234 and the outer edge 232. In some embodiments, the width dimension 239 may be between about 1 millimeter and about 2 millimeters. For example, in at least one such embodiment, the width dimension 239 may be between 1.3 millimeters and 2.3 millimeters, such as 1.8 millimeters.

Moreover, the tab portion 230 of the substrate 210 may comprise a variety of materials. In some embodiments, the tab portion 230 may comprise the same material as the loop portion 220. However, in other embodiments, the tab portion 230 may comprise a different material than the loop portion 220. The tab portion 230 may comprise any of the materials that the loop portion 220 may comprise as described herein.

The substrate 210 may be formed in a variety of ways. For instance, in some embodiments, forming the substrate 210 may involve laser cutting the loop portion 220 of the substrate 210 and/or the tab portion 230 of the substrate 210. Moreover, in some embodiments, forming the substrate 210 may involve etching the loop portion 220 of the substrate 210 and/or the tab portion 230 of the substrate 210.

In some embodiments, the substrate 210 may be substantially planar. The term "substantially planar," as used in this disclosure, refers to exactly planar or one or more deviations from exactly planar that do not significantly impact comfort of a wearer of an eye-mountable device and power delivery of an antenna of the eye-mountable device as described herein.

In addition, in some embodiments, forming the substrate 210 may involve bending the substrate 210 to a curvature, such as a curvature of a transparent polymer. And in at least one such embodiment, bending the substrate 210 may involve applying a force and/or a torque to one or more portions of the substrate 210, such as the loop portion 220 and/or the tab portion 230.

IV. Example Structures and Devices

Figure 3A:
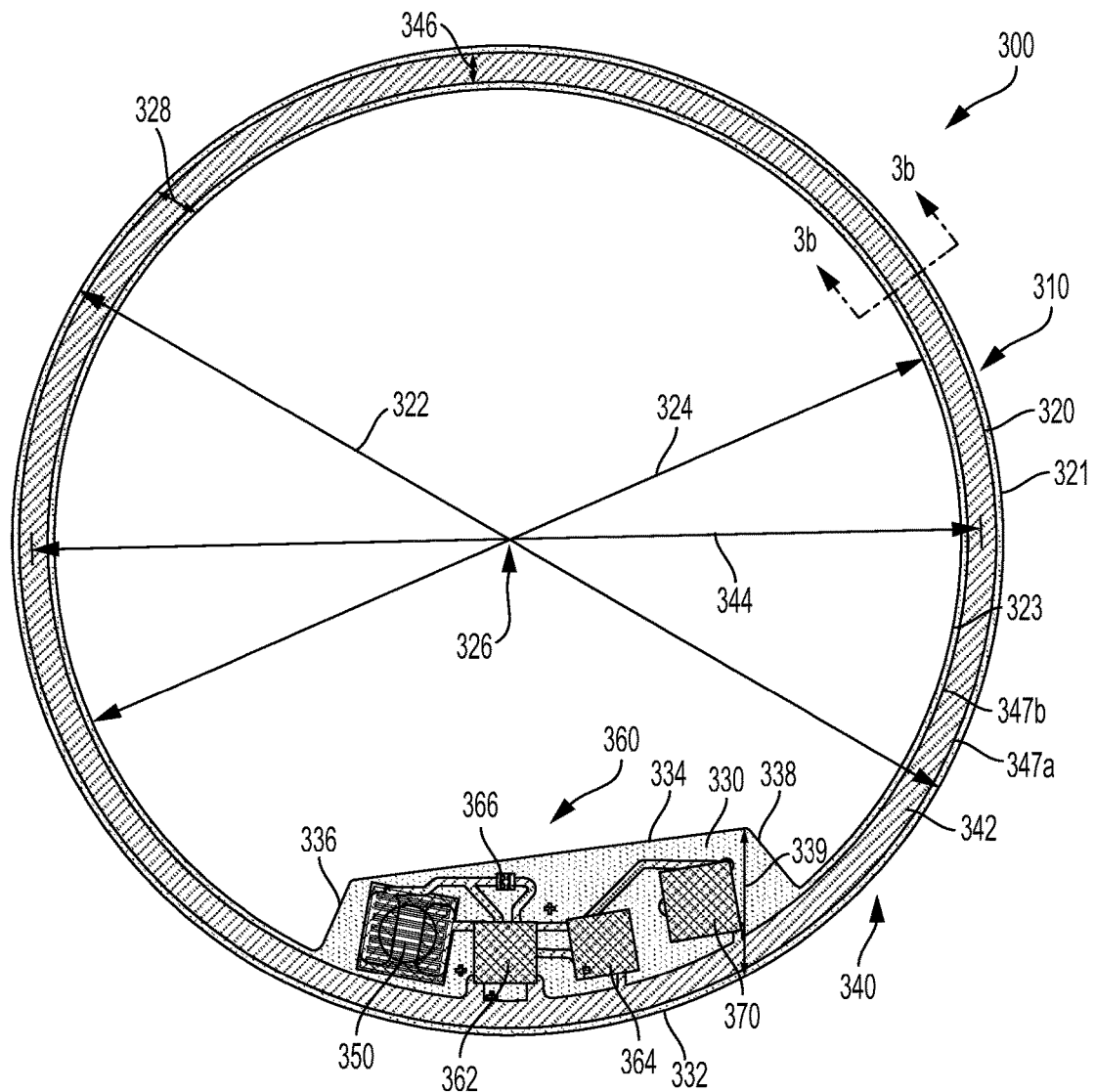
FIG. 3a is a top view of a structure, according to an example embodiment.

A structure may include one or more components disposed on a substrate, such as substrate 210 shown in FIG. 2. FIG. 3a is a top view of a structure 300, according to an example embodiment. The structure 300 may include a substrate 310, an antenna 340, and a sensor 350. Moreover, as shown in FIG. 3a, in some embodiments, the structure 300 may further include electronics 360. Further, as shown in FIG. 3a, in some embodiments, the structure 300 may further include a battery 370.

The substrate 310 may include a loop portion 320 and a tab portion 330. The loop portion 320 of the substrate 310 may have an outer circumference 321 defined by an outer diameter 322 and an inner circumference 323 defined by an inner diameter 324. Moreover, the loop portion 320 may have a center 326. Further, the loop portion 320 may have a width dimension 328. The tab portion 330 of the substrate 310 may extend from the inner circumference 323 of the loop portion 320 towards the center 326 of the loop portion 320. Further, the tab portion 330 of the substrate 310 may include an outer edge 332 corresponding to the outer circumference 321 of the loop portion 320, an inner edge 334 opposite the outer edge 332, and a first side edge 336 and a second side edge 338 that each extend inwardly from the inner circumference 323 of the loop portion 320 to the inner edge 334 of the tab portion 330. Further still, in some embodiments, the first side 336 and the second side 338 of the tab portion 330 may be substantially perpendicular to the inner circumference 323 of the loop portion 320. Moreover, the tab portion 330 may have a width dimension 339.

The substrate 310 may take the form of or be similar in form to the substrate 210. For instance, the loop portion 320 may take the form of or be similar in form to the loop portion 220, and the tab portion 330 may take the form of or be similar in form to the tab portion 230.

Accordingly, the outer circumference 321 may take the form of or be similar in form to the outer circumference 221, the outer diameter 322 may take the form of or be similar in form to the outer diameter 222, the inner circumference 323 may take the form of or be similar in form to the inner circumference 223, the inner diameter 324 may take the form of or be similar in form to the inner diameter 224, the center 326 may take the form of or be similar in form to the center 226, the width dimension 328 may take the form of or be similar in form to the width dimension 228, the outer edge 332 may take the form of or be similar in form to the outer edge 232, the inner edge 334 may take the form of or be similar in form to the inner edge 234, the first side edge 336 may take the form of or be similar in form to the first side edge 236, the second side edge 338 may take the form of or be similar in form to the second side edge 238, and the width dimension 339 may take the form of or be similar in form to the width dimension 239.

Moreover, the antenna 340 may include a conductive loop 342, and the conductive loop 342 may be disposed on the loop portion 320 of the substrate 310 between the inner circumference 323 and the outer circumference 321 of the loop portion 320. The antenna 340 may be configured for communications and/or harvesting energy as described herein.

The conductive loop 342 may have a variety of dimensions. For instance, in some embodiments, the conductive loop 342 may have a center diameter 344 between 9.65 millimeters and 11.65 millimeters, such as 10.65 millimeters. Further, in some embodiments, the center diameter 344 may be selected to be less than a portion of the eye of a wearer of an eye-mountable device, such as the limbus of the eye of the wearer of the eye-mountable device. Further still, in some embodiments, the conductive loop 342 may have a width dimension 346 between 250 micrometers and 350 micrometers, such as 300 micrometers. In some embodiments, the conductive loop 342 may comprise a continuous strip of conductive material that wraps entirely around the loop portion 320 of the substrate 310.

In addition, the conductive loop 342 may have an outer circumference 347a defined by an outer diameter (not labeled in FIG. 3a) and an inner circumference 347b defined by an inner diameter (not labeled in FIG. 3a). The outer diameter of the conductive loop 342 may be based on the center diameter 344 and width dimension 346 of the conductive loop 342. For instance, in some embodiments, the outer diameter may be between 9.52 millimeters and 11.40 millimeters, such as 10.58 millimeters. Moreover, the inner diameter of the conductive loop 342 may be based on the center diameter 344 and the width dimension 346 of the conductive loop 342. For instance, in some embodiments, the inner diameter may be between 9.53 millimeters and 11.50 millimeters, such as 10.61 millimeters. Further, in some embodiments, the outer diameter and/or the inner diameter may be selected to be less than a portion of the eye of a wearer of an eye-mountable device, such as the limbus of the eye of the wearer of the eye-mountable device.

Figure 3B:
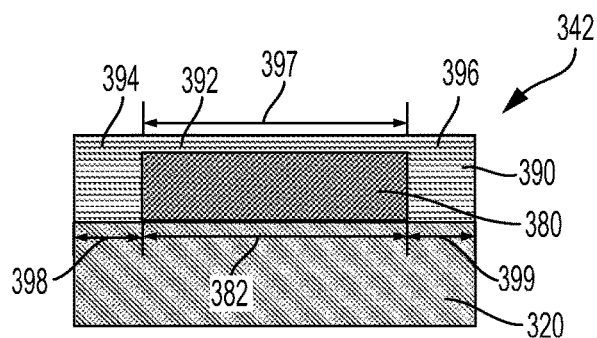
FIG. 3b is a side cross-section view of a structure shown in FIG. 3a, according to an example embodiment.

Further, the conductive loop 342 may comprise a variety of materials. For instance, in some embodiments, the conductive loop 342 may include a metal layer coated with a barrier layer. FIG. 3b is a side cross-section view of the structure 300, according to an example embodiment. As shown in FIG. 3b, the conductive loop 342 may include a metal layer 380 coated with a barrier layer 390. The metal layer 380 may be disposed on the loop portion 320 of the substrate 310, a first portion 392 of the barrier layer 390 may be disposed on the metal layer 380, and a second portion 394 and a third portion 396 of the barrier layer 390 may be disposed on the loop portion 320 of the substrate 310. The first portion 392 may have a width dimension 397, the second portion 394 may have a width dimension 398, and the third portion 396 may have a width dimension 399.

The metal layer 380 may take various different forms in various different embodiments. For instance, in some embodiments, the metal layer 380 may comprise aluminium, gold, titanium, chrome, tantalum, and/or platinum. Moreover, in some embodiments, the metal layer 380 may have a thickness between 5 micrometers and 10 micrometers, such as 9 micrometers. Further still, in some embodiments, the metal layer 380 may have a width dimension 382 between 250 micrometers and 350 micrometers, such as 300 micrometers.

In addition, the barrier layer 390 may take various different forms in various different embodiments. For instance, in some embodiments, the barrier layer 390 may comprise one or more polymer layers. And in at least one such embodiment, the barrier layer 390 may comprise paralyene, PET, silicone (e.g., spray coated silicone), and/or cyclical olefin copolymers. Further, in some embodiments, the barrier layer 390 may have thickness between a few nanometers and 20 micrometers, such as less than 5 nanometers, between 2 micrometers and 3 micrometers, between 10 micrometers and 15 micrometers, and between 10 micrometers and 20 micrometers. For instance, in some embodiments, the barrier layer 390 may have a thickness of 3 micrometers.

In some embodiments, barrier layer 390 may comprise the same material as the loop portion 320 of the substrate 310. However, in other embodiments, the barrier layer 390 may comprise a different material than the loop portion 220. Further, in some embodiments, the barrier layer 390 may comprise the same material as the tab portion 330 of the substrate 310. However, in other embodiments, the barrier layer 390 may comprise a different material than the tab portion 330. The barrier layer 390 may comprise any of the materials that the loop portion 320 and/or tab portion 330 may comprise as described herein.

As noted above, the first portion 392 of the barrier layer 390 may be disposed on the metal layer 380, and the second portion 394 and the third portion 396 of the barrier layer 390 may be disposed on the loop portion 320 of the substrate 310. With this arrangement, the barrier layer 390 may cover the metal layer 380 and extend from the metal layer 380. Accordingly, with this arrangement, the metal layer 380 may be encapsulated by the barrier layer 390 and the loop portion 320 of the substrate 310. The barrier layer 390 may help protect the metal layer 380 from moisture.

In some embodiments, the barrier layer 390 may extend from the metal layer 380 a distance that is substantially equal to the width dimension 398 of the second portion 394 of the barrier layer 390. And in at least one such embodiment, the width dimension 398 of the second portion 394 of the barrier layer 390 may be between 25 micrometers and 125 micrometers, such as 75 micrometers. The term "substantially equal," as used in this disclosure refers to exactly equal or one or more deviations from exactly equal that do not significantly impact comfort of a wearer of an eye-mountable device and power delivery of an antenna of the eye-mountable device as described herein.

Moreover, in some embodiments, the width dimension 399 of the third portion 394 of the barrier layer 390 may be substantially equal to the width dimension 398 of the second portion 394. However, in other embodiments, the width dimension 399 of the third portion 394 of the barrier layer 390 may be different than the width dimension 398 of the second portion 396 of the barrier layer 390. The width dimension 398 of the second portion 396 of the barrier layer 390 and/or width dimension 399 of the third portion 398 of the barrier layer 390 may be based on the width dimension 328 of the loop substrate 320 of the substrate 310 and/or the width dimension 382 of the metal layer 380. In addition, in some embodiments, the width dimension 397 may be substantially equal to the width dimension 382 of the metal layer 380.

Although in the example described above the first portion 392 of the barrier layer 390 may be disposed on the metal layer 380 and the second portion 394 and the third portion 396 of the barrier layer 390 may be disposed on the loop portion 392 of the substrate, in other examples, at least some of the first portion 392 of the barrier layer 390 may be disposed on the loop portion 320, at least some of the second portion 394 may be disposed on the metal layer 380, and/or at least some of the third portion 396 may be disposed on the metal layer 380.

Further, the sensor 350 may be disposed on the tab portion 330 of the substrate 310. With this arrangement, the sensor 350 may be located inside of the conductive loop 342. The sensor 350 may be configured to detect an analyte, such as an analyte in a tear film of a user wearing an eye-mountable device. In some embodiments, the sensor 350 may take the form of a working electrode and a reference electrode in an interdigitated arrangement.

Further still, the electronics 360 may be disposed on the tab portion 330 of the substrate 310. With this arrangement, the electronics 360 may be located inside of the conductive loop 342. The electronics 360 may include a controller 362, a capacitor 364, and a light emitting diode 366.

The controller 362 may take the form of an application specific integrated circuit (ASIC) and be configured to operate the sensor 350 and/or the antenna 340. Moreover, the capacitor 364 may be configured to stabilize a DC voltage that is provided to the controller 362. Further, the light emitting diode 366 may be configured to emit and/or transmit light to be perceived by the eye of a user wearing an eye-mountable device.

Moreover, the battery 370 may be disposed on the tab portion 330 of the substrate 310. With this arrangement, the battery 370 may be located inside of the conductive loop 342. The battery 370 may be configured to provide electrical power to the controller 362. In some embodiments, the battery 370 may take the form of a solid-state lithium battery. Moreover, in some embodiments, the battery 370 may be a re-chargeable battery. Further, in some embodiments, the battery 370 may be a single-use battery.

The sensor 350, electronics 360, and battery 370 may be disposed on the tab portion 330 of the substrate 310 in a variety of ways. FIG. 3c is a partial top view of the structure 300, according to an example embodiment. In particular, FIG. 3c is a top view of the sensor 350, electronics 360, and battery 370 disposed on the tab portion 330 of the substrate 310.

In some embodiments, the sensor 350, controller 362, capacitor 364, light emitting diode 366, and battery 370 may each have an area of less than one millimeter squared. For instance, in at least one such embodiment, the sensor 350, controller 362, capacitor 364, and battery 370 may each take the form of a square having a first dimension that is 850 micrometers and a second dimension that is 850 micrometers. With this arrangement, the controller 362 may be spaced apart from the capacitor 364 a distance 372. In some embodiments, the distance 372 may be between 0.9 millimeters and 1.3 millimeters, such as 1.1 millimeters. The distance 372 may be specified in a variety of ways. For example, as shown in FIG. 3c, the distance 372 may be specified as a distance between a center of the controller 362 and a center of the capacitor 364. As another example, the distance 372 may be specified as a distance between an edge of the controller 362 and an edge of the capacitor 364. In some embodiments, the distance 372 may be selected based on one or more parameters of the tab portion 330 of the substrate 310, such as the width dimension 339 of the tab portion 330.

Moreover, the sensor 350 may be spaced apart from the controller 362 a distance 374. In some embodiments, the distance 374 may be substantially equal to the distance 372. However, in other embodiments, the distance 374 may be different than the distance 372. The distance 374 may be specified in a variety of ways. For example, as shown in FIG. 3c, the distance 374 may be specified as a distance between a center of the sensor 350 and a center of the controller 362. As another example, the distance 372 may be specified as a distance between an edge of the controller 362 and an edge of the capacitor 364. In some embodiments, the distance 374 may be selected based on one or more parameters of the tab portion 330 of the substrate 310, such as the width dimension 339 of the tab portion 330.

Further, the capacitor 362 may be spaced apart from the battery 370 a distance 376. In some embodiments, the distance 376 may be substantially equal to the distance 372 and/or the distance 374. However, in other embodiments, the distance 376 may be different than the distance 372 and/or the distance 374. The distance 374 may be specified in a variety of ways. For example, as shown in FIG. 3c, the distance 376 may be specified as a distance between a center of the capacitor 364 and a center of the batter 370. As another example, the distance 372 may be specified as a distance between an edge of the capacitor 364 and an edge of the battery 370. In some embodiments, the distance 376 may be selected based on one or more parameters of the tab portion 330 of the substrate 310, such as the width dimension 339 of the tab portion 330.

The sensor 350, the electronics 360, and the battery 370 may be connected by interconnects. For instance, the sensor 350 may be connected to the controller 362 via first interconnects 368a and 368b, and may be connected to the light emitting diode 366 via the first interconnect 368b. The controller 362 in turn may be connected to the light emitting diode 366 via first interconnect 368c, and may be connected to the capacitor 364 via first interconnects 368d and 368e. And the capacitor 364 may be connected to the battery 370 via first interconnect 368f.

In addition, the sensor 350, the electronics 360, and the battery 370 may be connected to the conductive loop 342 via interconnects. And in embodiments where the conductive loop 342 comprises the metal layer 380, the sensor 350, the electronics 360, and the battery 370 may be connected to the metal layer 380 via the interconnects. For instance, the sensor 350 may be connected to the conductive loop 342 via second interconnects 369a and 369b, the capacitor 364 may be connected to the conductive loop 342 via second interconnect 369c, and the battery 370 may be connected to the conductive loop 342 via the second interconnect 369d.

The first interconnects 368a-f and the second interconnects 369a-d may each take the form of one or more wires. Moreover, the first interconnects 368a-f and the second interconnects 369a-d may comprise a variety of materials. For instance, in some embodiments, the first interconnects 368a-f and the second interconnects 369a-d may comprise the same material as the metal layer 380. However, in other embodiments, the first interconnects 368a-f and the second interconnects 369a-d may comprise a different material than the metal layer 380. The first interconnects 368a-f and the second interconnects 369a-d may comprise any material that the metal layer 380 may comprise as described herein.

Further, in some embodiments, two or more interconnects of the first interconnects 368a-f may comprise the same material. Further still, in some embodiments, two or more interconnects of the second interconnects 369a-d may comprise the same material. Moreover, in some embodiments, at least one interconnect of the first interconnects 368a-f may comprise the same material as at least one interconnect of the second interconnects 369a-d. However, in other embodiments, the first interconnects 368a-f may comprise a different material than the second interconnects 369a-d.

Moreover, in some embodiments, the sensor 350, electronics 360, and/or battery 370 may be coated with a barrier layer. FIG. 3d is a side cross-section view of the structure 300, according to an example embodiment. As shown in FIG. 3d, the controller 362, the capacitor 364, and the battery 370 may be disposed on the tab portion 330 of the substrate 310, and a barrier layer 390' may coat the controller 362, the capacitor 364, and the battery 370. With this arrangement, the barrier layer 390' may cover the controller 362, the capacitor 364, and the battery 370 and extend from the controller 362, the capacitor 362, and the battery 370. Accordingly, with this arrangement, the controller 362, the capacitor 364, and the battery 370 may be encapsulated by the barrier layer 390' and the tab portion 330 of the substrate 310. The barrier layer 390' may help protect the controller 362, the capacitor 364, and the battery 370 from moisture.

In addition, in some embodiments, the light emitting diode 366, first interconnects 368a-f, and second interconnects 369a-d may be coated with the barrier layer 390' (not shown in FIG. 3d). With this arrangement, the barrier layer 390' may cover the light emitting diode 366, first interconnects 368a-f, and second interconnects 369a-d and extend from the light emitting diode 366, first interconnects 368a-f, and second interconnects 369a-d. Accordingly, with this arrangement, the light emitting diode 366, first interconnects 368a-f, and second interconnects 369a-d may be encapsulated by the barrier layer 390' and the tab portion 330 of the substrate 310. The barrier layer 390' may help to protect the light emitting diode 366, first interconnects 368a-f, and second interconnects 369a-d from moisture.

Further, as shown in FIG. 3d, the sensor 350 may be disposed on the tab portion 330 of the substrate 310 and the barrier layer 390' may at least partially coat the sensor 350. For instance, the barrier layer 390' may coat the sensor 350, except that there may be an opening 392' in the barrier layer 390' that is located over the sensor 350. The sensor 350 may be configured to receive analyte via the opening 392'. With this arrangement, the barrier layer 390' may partially cover the sensor 350 and extend from the sensor 350. Accordingly, with this arrangement, the barrier layer 390' may help to protect the sensor 392' from at least some moisture.

The barrier layer 390' may take the form of or be similar in form to the barrier layer 390. In some embodiments, the barrier layer 390 may comprise the same material as the barrier layer 390. However, in other embodiments, the barrier layer 390' may comprise a different material than the barrier layer 390. The barrier layer 390' may comprise any of the materials that the barrier layer 390 may comprise as described herein.

The structure 300 may be formed in a variety of ways. For instance, in some embodiments, forming the structure 300 may involve bonding the electronics 360 and battery 370 to the tab portion 330 of the substrate 310. Moreover, in some embodiments, forming the structure 300 may involve laser cutting the loop portion 320 of the substrate 310, the tab portion 330 of the substrate 310, and/or the opening 392' in the barrier layer 390'. Additionally or alternatively, forming the structure 300 may involve etching the loop portion 320 of the substrate 310, the tab portion 330 of the substrate 310, and/or the opening 392' in the barrier layer 390'. Further, in some embodiments, forming the structure 300 may involve one or more roll-to-roll manufacturing processes.

In some embodiments, the structure 300 may be substantially planar. In addition, in some embodiments, forming the structure 300 may involve bending the structure 300 to a curvature, such as a curvature of a transparent polymer. And in at least one such embodiment, bending the structure 300 may involve applying a force and/or a torque to one or more portions of the structure, such as the loop portion 320 of the substrate 310 and/or the tab portion 330 of the substrate 310.

Although in the example described above the structure 300 includes the battery 370, in other examples, a structure may not include the battery 370. In some such examples, the antenna 340 may harvest energy and use the harvested energy to provide electrical power to the controller 362.

The structure 300 may be configured to be embedded in a transparent polymer, where the transparent polymer may define a posterior side and an anterior side of an eye-mountable device, where the transparent polymer may have a concave surface and a convex surface, and where the concave surface may be configured to be removably mounted over a corneal surface and the convex surface may be configured to be compatible with eyelid motion when the concave surface is so mounted.

In some embodiments, the center diameter 344 of the conductive loop 342, the width dimension 346 of the conductive loop 342, and the width dimension 339 of the tab portion 330 of the substrate 310 may be selected based on a predetermined comfort of a wearer of an eye-mountable device and/or power delivery of the antenna 340.

Further, in some embodiments, the center diameter 344 of the conductive loop 342, the width dimension 346 of the conductive loop, the width dimension 339 of the tab portion 330 of the substrate 310, the width dimension 398 of the second portion 394 of the barrier layer 390 and/or the width dimension 399 of the third portion 396, and the distance 372, the distance 374, and/or the distance 376 may be selected based on a predetermined comfort of a wearer of an eye-mountable device and/or power delivery of the antenna 340.

In addition, in some embodiments, the structure 300 may further include an adhesive. Moreover, in some embodiments, the adhesive may be located between the loop portion 320 of the substrate 310 and the metal layer 380. Further, in some embodiments, the adhesive may be located between the tab portion 330 of the substrate 310 and one or more components, such as the controller 362, capacitor 364, light emitting diode 366, and/or battery 370. Further still, in some embodiments, the adhesive may comprise polyurethane. Moreover, in some embodiments, the adhesive may have a thickness of about 2 micrometers.

The structure 300 may have a variety of thicknesses. For instance, in some embodiments, the structure 300 may have a thickness between 25 micrometers to 60 micrometers, such as about 40 micrometers. Moreover, in some embodiments, the thickness of the structure 300 may be based at least in part on a thickness of one or more components of the structure, such as a thickness of the loop portion 320 of the substrate 310, a thickness of an adhesive, a thickness of the metal layer 380, and/or a thickness of the barrier layer 390.

Figure 4A:
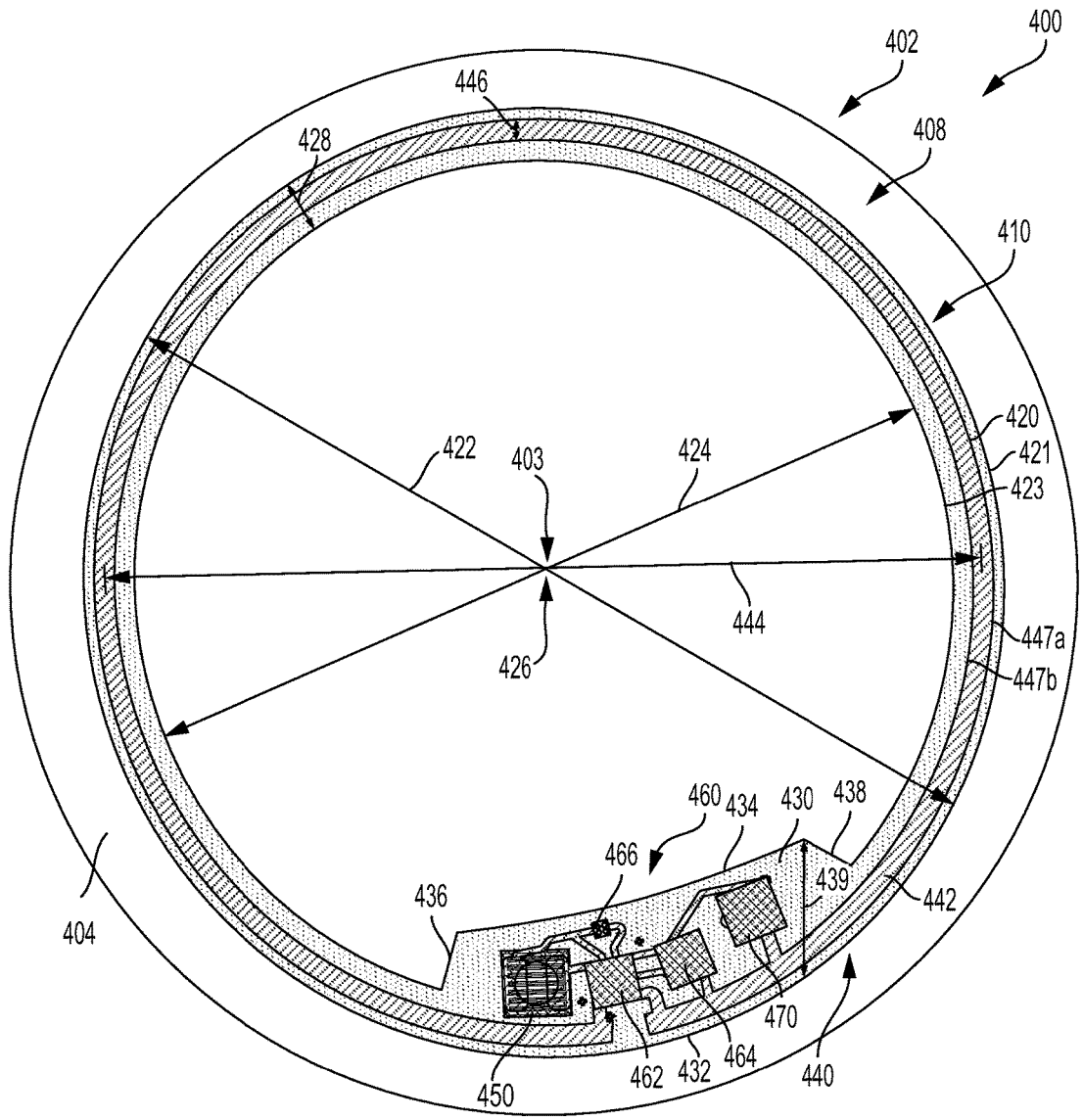
FIG. 4a is a top view of an eye-mountable device, according to an example embodiment.
Figure 4B:
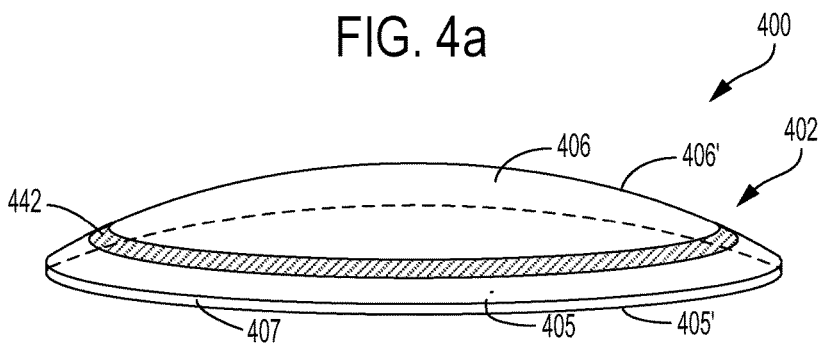
FIG. 4b is a side view of the eye-mountable device shown in FIG. 4a, according to an example embodiment.

FIG. 4a is a top view of an eye-mountable electronic device 400, according to an example embodiment. FIG. 4b is a side view of the eye-mountable electronic device 400 shown in FIG. 4a, according to an example embodiment. As shown in FIG. 4a, the eye-mountable device 400 may include a transparent polymer 402 and a structure 408 embedded in the transparent polymer 402. The eye-mountable device 400 could take the form of or be similar in form to the eye-mountable device 110 shown in FIG. 1.

The transparent polymer 402 may be shaped as a curved disk. The transparent polymer 402 can be a substantially transparent material to allow incident light to be transmitted to the eye while the eye-mountable device 400 is mounted to the eye. The transparent polymer 402 can be a biocompatible material similar to those employed to form vision correction and/or cosmetic contact lenses in optometry, such as PET, polymethyl methacrylate ("PMMA"), silicone hydrogels, combinations of these, etc. The transparent polymer 402 could take the form of or be similar in form to the polymeric material 120.

Further, the transparent polymer 402 may have a concave surface 405 and a convex surface 406. The concave surface 405 may be configured to be removably mounted over a corneal surface and the convex surface 406 may be configured to be compatible with eyelid motion when the concave surface 405 is so mounted. With this arrangement, the transparent polymer 402 may define a posterior side 405' of the eye-mountable device 400 and an anterior side 406' of the eye-mountable device 400. The anterior side 406' may be opposite the posterior side 405'. A circular outer side edge 407 of the transparent polymer 402 may connect the concave surface 405 and the convex surface 406.

The eye-mountable device 400 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 400 can be selected according to the size and/or shape of the corneal surface and/or the scleral surface of the wearer's eye.

While the eye-mountable device 400 is mounted in an eye, the anterior side 406' faces outward to the ambient environment while the posterior side 405' faces inward, toward the corneal surface. The anterior side 406' can therefore be considered an outer, top side of the eye-mountable device 400 whereas the posterior side 405' can be considered an inner, bottom side. The "top" view shown in FIG. 4a is facing the anterior side 406'.

The structure 408 may include a substrate 410, an antenna 440, and a sensor 450. Moreover, as shown in FIG. 4a, in some embodiments, the structure 408 may further include electronics 460. Further, as shown in FIG. 4a, in some embodiments, the structure 408 may further include a battery 470.

The substrate 410 may include a loop portion 420 and a tab portion 430. The loop portion 420 of the substrate 410 may have an outer circumference 421 defined by an outer diameter 422 and an inner circumference 423 defined by an inner diameter 424. Moreover, the loop portion 420 may have a center 426. Further, the loop portion 420 may have a width dimension 428. The tab portion 430 of the substrate 410 may extend from the inner circumference 423 of the loop portion 420 towards the center 426 of the loop portion 420. Further, the tab portion 430 of the substrate 410 may include an outer edge 432 corresponding to the outer circumference 421 of the loop portion 420, an inner edge 434 opposite the outer edge 432, and a first side edge 436 and a second side edge 438 that each extend inwardly from the inner circumference 423 of the loop portion 420 to the inner edge 434 of the tab portion 430. Further still, in some embodiments, the first side 436 and the second side 438 of the tab portion 430 are substantially perpendicular to the inner circumference 423 of the loop portion 420. Moreover, the tab portion 430 may have a width dimension 439.

The substrate 410 may take the form of or be similar in form to the substrate 310 and/or the substrate 210. For instance, the loop portion 420 may take the form of or be similar in form to the loop portion 320 and/or the loop portion 220, and the tab portion 430 may take the form of or be similar in form to the tab portion 330 and/or the tab portion 230.

Accordingly, the outer circumference 421 may take the form of or be similar in form to the outer circumference 321 and/or the outer circumference 221, the outer diameter 422 may take the form of or be similar in form to the outer diameter 322 and/or the outer diameter 222, the inner circumference 423 may take the form of or be similar in form to the inner circumference 323 and/or the inner circumference 233, the inner diameter 424 may take the form of or be similar in form to the inner diameter 324 and/or the inner diameter 224, the center 426 may take the form of or be similar in form to the center 326 and/or the center 226, the width dimension 428 may take the form of or be similar in form to the width dimension 328 and/or the width dimension 228, the outer edge 432 may take the form of or be similar in form to the outer edge 332 and/or the outer edge 232, the inner edge 434 may take the form of or be similar in form to the inner edge 334 and/or the inner edge 234, the first side edge 436 may take the form of or be similar in form to the first side edge 336 and/or the first side edge 236, the second side edge 438 may take the form of or be similar in form to the second side edge 328 and/or the second side edge 238, and the width dimension 439 may take the form of or be similar in form to the width dimension 339 and/or the width dimension 239.

Moreover, the antenna 440 may include a conductive loop 442, and the conductive loop 442 may be disposed on the loop portion 420 of the substrate 410 between the inner circumference 423 and the outer circumference 421 of the loop portion 420. The antenna 440 may be configured for communications and/or harvesting energy as described herein. The conductive loop 442 may have a center diameter 444, a width dimension 446, an outer circumference 447a defined by an outer diameter (not labeled in FIG. 4a), and an inner circumference 447b defined by an inner diameter (not labeled in FIG. 4a).

The antenna 440 may take the form of or be similar in form to the antenna 330, and the conductive loop 442 may take the form of or be similar in form to the conductive loop 342. Accordingly, the center diameter 444 may take the form of or be similar in form to the center diameter 344, the width dimension 446 may take the form of or be similar in form to the width dimension 346, the outer circumference 447a defined by the outer diameter may take the form of or be similar in form to the outer circumference 347a defined by the outer diameter, and the inner circumference 447b may take the form of or be similar in form to the inner circumference 347b defined by the inner diameter.

Further, the sensor 450 may be disposed on the tab portion 430 of the substrate 410. With this arrangement, the sensor 450 may be located inside of the conductive loop 442. The sensor 450 may be configured to detect an analyte, such as an analyte in a tear film of a user wearing an eye-mountable device. The sensor 450 may take the form of or be similar in form to the sensor 350. In some embodiments, the anterior side 406' of the transparent polymer 402 may include a channel, and the sensor may be configured to receive the analyte via the channel.

Further still, the electronics 460 may be disposed on the tab portion 430 of the substrate 410. With this arrangement, the electronics 460 may be located inside of the conductive loop 442. The electronics 460 may include a controller 462, a capacitor 464, and a light emitting diode 466. The controller 462 may be configured to operate the sensor 450 and/or the antenna 440, the capacitor 464 may be configured to stabilize a DC voltage that is provided to the controller 462, and the light emitting diode 466 may be configured to emit and/or transmit light to be perceived by the eye of a user wearing the eye-mountable device 400. The controller 462 may take the form of or be similar in form to the controller 362, the capacitor 464 may take the form of or be similar in form to the capacitor 364, and the light emitting diode 466 may take the form of or be similar in form to the light emitting diode 366.

Moreover, the battery 470 may be disposed on the tab portion 430 of the substrate 410. With this arrangement, the battery 470 may be located inside of the conductive loop 442. The battery 470 may be configured to provide electrical power to the controller 462. The battery 470 may take the form of or be similar in form to the battery 370.

The sensor 450, electronics 460, and battery 470 are disposed on the tab portion 430 of the substrate 410 in the same or similar way as the sensor 350, electronics 360, and battery 370 are disposed on the tab portion 330 of the substrate 310. Moreover, the sensor 450, electronics 460, and battery 470 are connected via interconnects in the same or similar way as the sensor 350, electronics 360, and battery 370 are connected via the first interconnects 368a-f. Further, the sensor 450, electronics 460, and battery 470 are connected to the conductive loop 442 via interconnects in the same or similar way as the sensor 350, electronics 360, and battery 370 are connected to the conductive loop 342 via the second interconnects 369a-d.

As noted, the structure 408 may be embedded in the transparent polymer 402. The structure 408 may be embedded to be situated along an outer periphery 404 of the transparent polymer 402, away from a center region 403. The structure 408 does not interfere with vision because it is too close to the eye to be in focus and is positioned away from the center region 403 where incident light is transmitted to the light sensing portions of the eye.

The structure 408 may be embedded in the transparent polymer 402 in a variety of ways. For instance, in some embodiments, the transparent polymer 402 may take the form of a first polymer layer and a second polymer. In some such embodiments, the structure 408 may be positioned on the first polymer layer and the second polymer layer may be formed over the first polymer layer and the structure 408. Moreover, in some embodiments, the transparent polymer 402 may take the form of one polymer layer. In some such embodiments, the polymer layer may be formed around the structure 408.

In some embodiments, the structure 408 may be substantially planar before being embedded in the transparent polymer 402. Moreover, in some embodiments, the structure 408 may be substantially planar after being embedded in the transparent polymer 402.

Further, in some embodiments, the structure 408 may at least partially conform to a curvature of the transparent polymer 402. For instance, in an example embodiment, the convex surface 406 of the transparent polymer 402 may have a curvature, and the structure 408 may at least partially conform to the curvature of the convex surface 406. Moreover, in an example embodiment, the concave surface 405 of the transparent polymer 402 may have a curvature, and the structure 408 may at least partially conform to the curvature of the concave surface 405. Further, in an example embodiment, a portion of the transparent polymer 402 between the anterior side 406' and the posterior side 405' of the eye-mountable device 400 may have a curvature, and the structure 408 may at least partially conform to the curvature of the portion of the transparent polymer 402.

Moreover, in some embodiments, embedding the structure 408 in the transparent polymer 402 may involve at least partially conforming the structure 408 to a curvature of the transparent polymer 402. For instance, in some embodiments, at least partially conforming the structure 408 to a curvature of the transparent polymer 402 may involve bending the structure 408 to the curvature. And in at least one such embodiment, bending the structure 408 may involve applying a force and/or a torque to one or more portions of the structure 408, such as the loop portion 420 of the substrate 410 and/or the tab portion 430 of the substrate 410.

In some embodiments, the center diameter 444 of the conductive loop 442, the width dimension 446 of the conductive loop 442, and the width dimension 439 of the tab portion 430 of the substrate 410 may be selected based on a predetermined comfort of a wearer of the eye-mountable device 400 and/or power delivery of the antenna 440.

Further, in some embodiments, the center diameter 444 of the conductive loop 442, the width dimension 446 of the conductive loop 442, the width dimension 439 of the tab portion 430 of the substrate 410 may be selected based on a predetermined comfort of a wearer of an eye-mountable device 400 and/or power delivery of the antenna 440.

Figure 5:
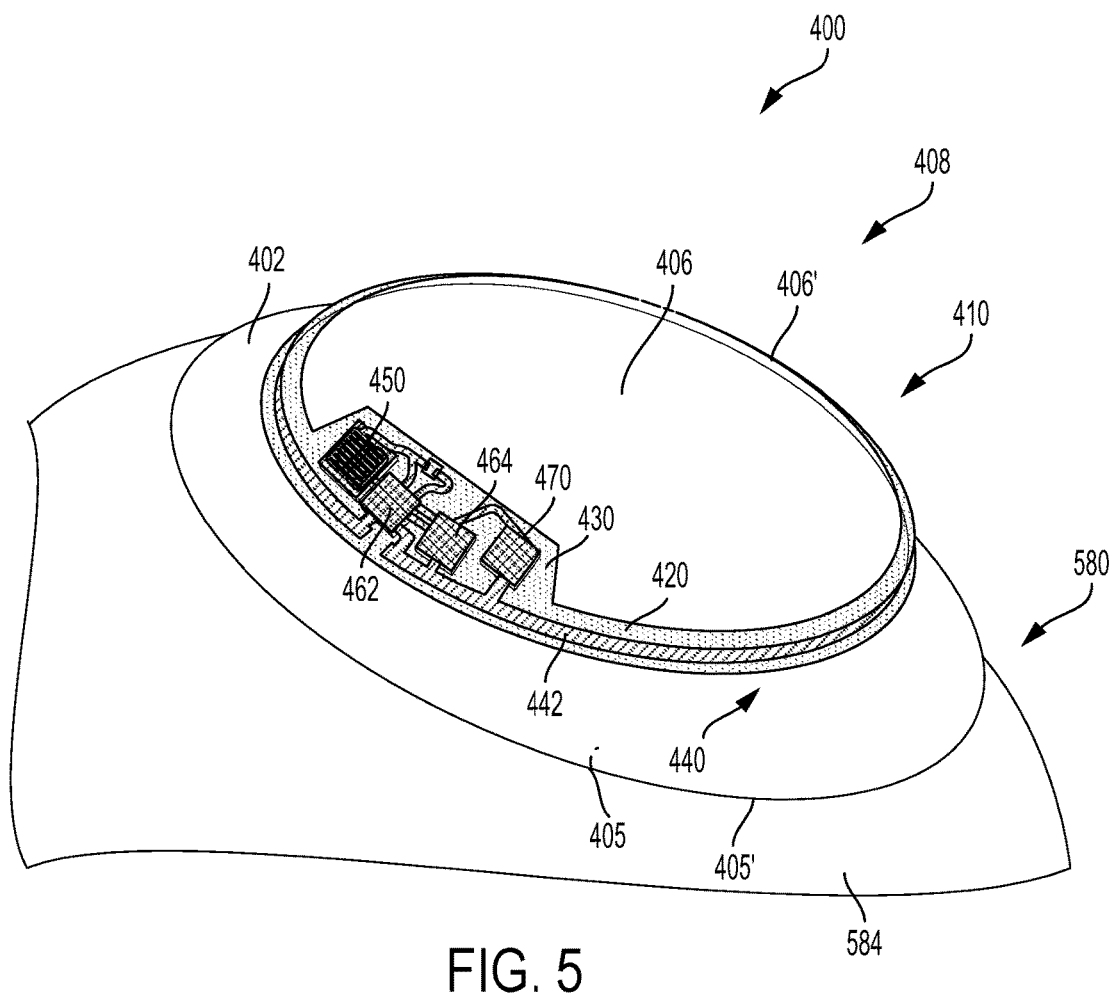
FIG. 5 is a perspective view of the eye-mountable device shown in FIG. 4a while mounted over a corneal surface of an eye, according to an example embodiment.

FIG. 5 is a perspective view of the eye-mountable device 400 mounted over a corneal surface 584 of an eye 580, according to an example embodiment. For purposes of illustration, only a portion of the corneal surface 584 is depicted in FIG. 5.

As shown in FIG. 5, the concave surface 405 of the transparent polymer 402 is mounted over the corneal surface 584. With this arrangement, the anterior side 406' of the eye-mountable device 400 is facing outward and thus not touching the eye 580, and the posterior side 405' of the eye-mountable device 400 is facing inward and thus touching the eye 580.

When the eye-mountable device 400 is mounted over the corneal surface 584, the sensor 450 may be configured to detect an analyte in a tear film of the eye 580. With this arrangement, the eye-mountable device 400 may be configured to monitor health-related information based on the detected analyte.

Figure 6:
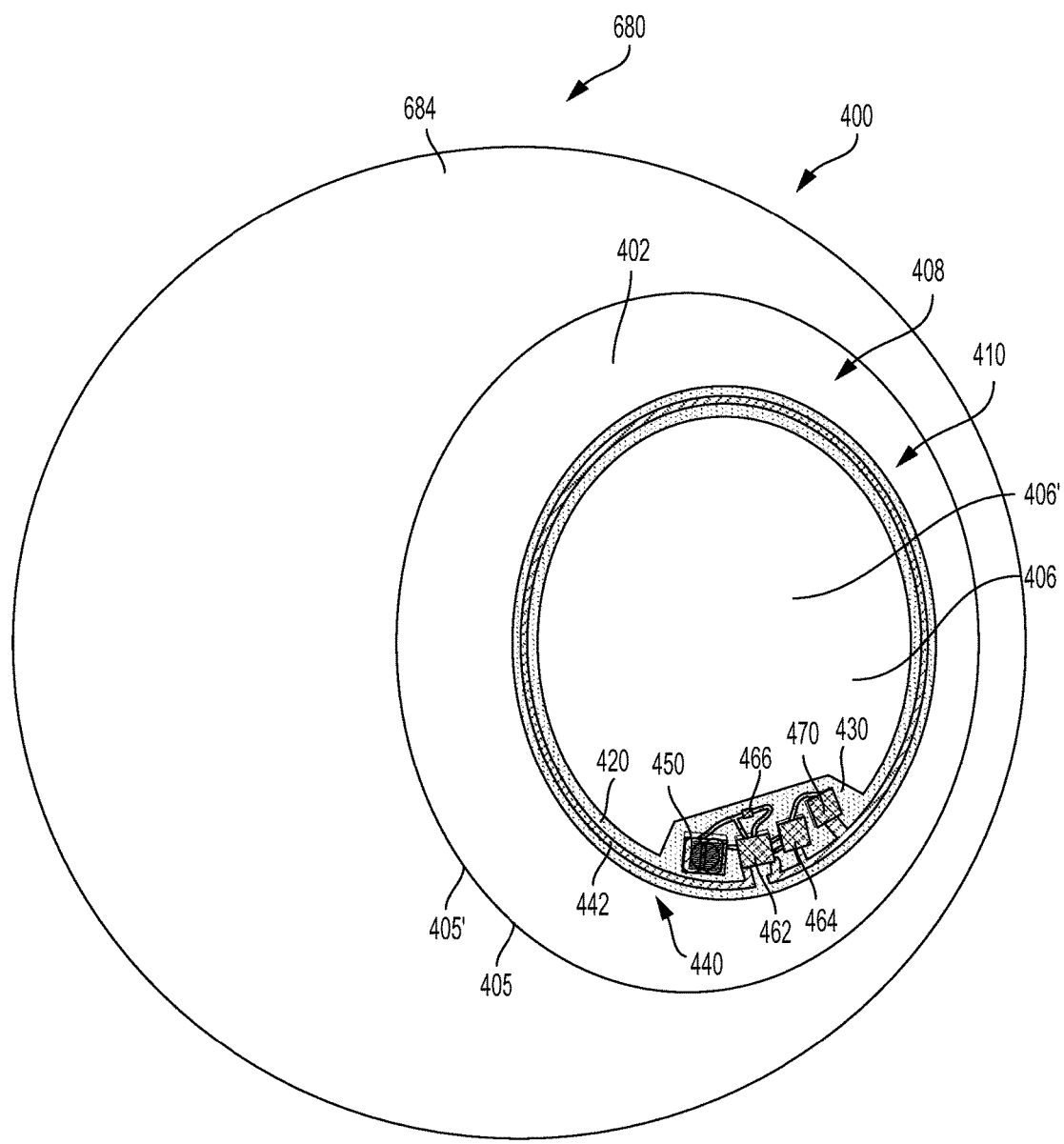
FIG. 6 is another perspective view of the eye-mountable shown in FIG. 4a while mounted over a corneal surface of an eye, according to an example embodiment.

FIG. 6 a perspective view of the eye-mountable device 400 mounted over a corneal surface 684 of an eye 680, according to an example embodiment.

As shown in FIG. 6, the concave surface 405 of the transparent polymer 402 is mounted over the corneal surface 684. With this arrangement, the anterior side 406' of the eye-mountable device 400 is facing outward and thus not touching the eye 680, and the posterior side 405' of the eye-mountable device is facing inward and thus touching the eye 680.

When the eye-mountable device 400 is mounted over the corneal surface 684, the sensor 450 may be configured to detect an analyte in a tear film of the eye 680. With this arrangement, the eye-mountable device 400 may be configured to monitor health-related information based on the detected analyte.

FIG. 7a is a side cross-section view of an eye-mountable electronic device 700 while mounted over a corneal surface 784 of an eye 780. FIG. 7b is a close-in side cross-section view enhanced to show tear film layers 790, 792 surrounding exposed surfaces 705, 706 of the eye-mountable device 700. As noted above, relative dimensions in the Figures are not necessarily to scale, but have been rendered for purposes of explanation only. In FIGS. 7a and 7b, for example, the total thickness of the eye-mountable device 700 can be about 200 micrometers, while the thickness of the tear film layers 790, 792 can each be about 10 micrometers, although this ratio may not be reflected in the drawings. Some aspects are exaggerated to allow for illustration and facilitate explanation.

The eye 780 includes a cornea 782 that is covered by bringing the upper eyelid 786 and lower eyelid 788 together over the top of the eye 780. Incident light is received by the eye 780 through the cornea 782, where light is optically directed to light sensing elements of the eye 780 (e.g., rods and cones, etc.) to stimulate visual perception. The motion of the eyelids 786, 788 distributes a tear film across the exposed corneal surface 784 of the eye 780. The tear film is an aqueous solution secreted by the lacrimal gland to protect and lubricate the eye 780. When the eye-mountable device 700 is mounted in the eye 780, the tear film coats both the convex and concave surfaces 705, 706 with an inner layer 790 (along the concave surface 705) and an outer layer 792 (along the convex surface 706). The tear film layers 790, 792 can be about 10 micrometers in thickness and together account for about 10 microliters.

The tear film layers 790, 792 are distributed across the corneal surface 784 and/or the convex surface 706 by motion of the eyelids 786, 788. For example, the eyelids 786, 788 raise and lower, respectively, to spread a small volume of tear film across the corneal surface 784 and/or the convex surface 706 of the eye-mountable device 700. The tear film layer 790 on the corneal surface 784 also facilitates mounting the eye-mountable device 700 by capillary forces between the concave surface 705 and the corneal surface 784. In some embodiments, the eye-mountable device 700 can also be held over the eye in part by vacuum forces against the corneal surface 784 due to the concave curvature of the eye-facing concave surface 705. In addition, the convex surface 706 may be configured to be compatible with eyelid motion when the concave surface 705 is mounted over the corneal surface 784.

As shown in FIGS. 7*a* and 7*b*, the eye-mountable device 700 may include a transparent polymer 702 and a structure 708 embedded in the transparent polymer 702. The transparent polymer 702 may include the concave surface 705 and the convex surface 706. The convex surface 706 may be configured to be removably mounted over the corneal surface 784, and the concave surface 705 may be configured to be compatible with eyelid motion when the concave surface is so mounted. With this arrangement, the transparent polymer 702 may define a posterior side 705' and an anterior side 706' of the eye-mountable device 700.

The structure 708 may include a substrate 710 that has a tab portion 730. A sensor 750 and a controller 762 may be connected via a first interconnect 768*a*, and the sensor 750, the controller 762, and the first interconnect 768*a* may be disposed on the tab portion 730 of the substrate 710. The controller 762 and first interconnect 768*a* may be coated with a barrier layer 790'. The sensor 750 may be configured to receive analyte from tear film 792 via a channel 772 to the sensor 750 through the transparent polymer 702. In addition, there may be an opening in the barrier layer 790' that is located over the sensor 750. In some embodiments, the barrier layer 790' may at least partially coat the sensor 750.

The eye-mountable device 700 may take the form of or be similar in form to the eye-mountable device 400, the transparent polymer 702 may take the form of or be similar in form to the transparent polymer 402, and the structure 708 may take the form of or be similar in form to the structure 408. In addition, the posterior side 705' may take the form of or be similar in form to the posterior side 405', the anterior side 706' may take the form of or be similar in form to the anterior side 406', the concave surface 705 may take the form of or be similar in form to the concave surface 405, the convex surface 706 may take the form of or be similar in form to the convex surface 406, the substrate 710 may take the form of or be similar in form to the substrate 210, the substrate 310, and/or the substrate 410, the tab portion 730 may take the form of or be similar in form to the tab portion 230, the tab portion 330, and/or the tab portion 430, the sensor 750 may take the form of or be similar in form to the sensor 350 and/or the sensor 450, the controller 762 may take the form of or be similar in form to the controller 362 and/or the controller 462, the first interconnect 768*a* may take the form of or be similar in form to the first interconnect 368*a*, and the barrier layer 790' may take the form of or be similar in form to the barrier layer 390'.

As shown in the cross-sectional views in FIGS. 7*a* and 7*b*, the structure 708 can be inclined such that the flat mounting surfaces of the structure 708 are approximately parallel to the adjacent portion of the convex surface 706'. As shown in FIG. 7*b*, the sensor 750, the controller 762, and the first interconnect 768*a* are disposed on the tab portion 730 of the substrate 710, such that the sensor 750 is facing the convex surface 706. In some embodiments, the sensor 750 may be at least 50 micrometers away from the convex surface 706 and may be a greater distance away from the concave surface 705. The sensor 750 could also be positioned closer to the concave surface 705 than the convex surface 706. With this arrangement, the sensor 750 can receive analyte concentrations in the tear film 792 through the channel 772.

Although structures described above may include a tab portion that has first and second side edges that that are substantially perpendicular to the inner circumference of the loop portion of the substrate, in other examples a structure may have an inner edge that has first and second ends that contact the inner circumference of the loop portion of the substrate.

Figure 8:
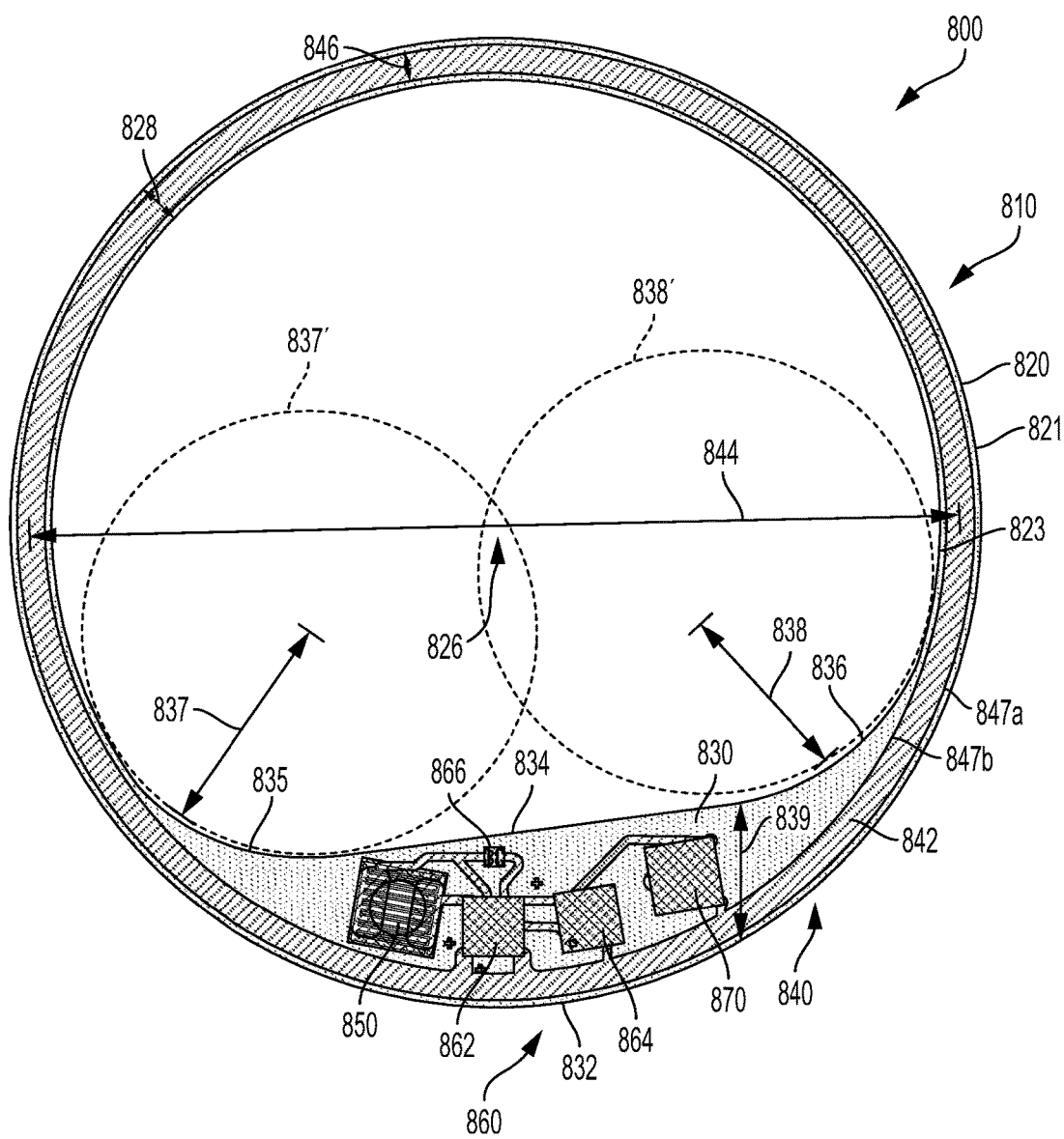
FIG. 8 is a top view of another structure, according to an example embodiment.

FIG. 8 is a top view of a structure 800, according to an example embodiment. The structure 800 may include a substrate 810, an antenna 840, and a sensor 850. Moreover, as shown in FIG. 8, in some embodiments, the structure 800 may further include electronics 860. Further, as shown in FIG. 8, in some embodiments, the structure 800 may further include a battery 870.

The substrate 810 may include a loop portion 820 and a tab portion 830. The loop portion 820 of the substrate 810 may have an outer circumference 821 defined by an outer diameter (not labeled in FIG. 8) and an inner circumference 823 defined by an inner diameter (not labeled in FIG. 8). Moreover, the loop portion 820 may have a center 826. Further, the loop portion 820 may have a width dimension 828.

The loop portion 820 of the substrate 810 may take the form of or be similar in form to the loop portion 220 of the substrate 210, the loop portion 320 of the substrate 310, and/or the loop portion 420 of the substrate 410. Accordingly, the outer circumference 421 may take the form of or be similar in form to the outer circumference 421, the outer circumference 321, and/or the outer circumference 221, the outer diameter may take the form of or be similar in form to the outer diameter 422, the outer diameter 322, and/or the outer diameter 222, the inner circumference 823 may take the form of or be similar in form to the inner circumference 423, the inner circumference 323, and/or the inner circumference 233, the inner diameter may take the form of or be similar in form to the inner diameter 424, the inner diameter 324, and/or the inner diameter 224, the center 826 may take the form of or be similar in form to the center 426, the center 326, and/or the center 226, and the width dimension 828 may take the form of or be similar in form to the width dimension 428, the width dimension 328, and/or the width dimension 228.

The tab portion 830 of the substrate 810 may extend from the inner circumference 823 of the loop portion 820 towards the center 826 of the loop portion 820. Further, the tab portion 830 of the substrate 810 may include an outer edge 832 corresponding to the outer circumference 821 of the loop portion 820, and an inner edge 834 opposite the outer edge 832. The inner edge 834 may include a first end 835 and a second end 836 that contact the inner circumference 823 of the loop portion 820 of the substrate 810.

In some embodiments, the first end 835 of the inner edge 834 may have a first curvature, and the second end 836 of the inner edge 384 may have a second curvature. Moreover, in some embodiments, the first curvature may have a first radius 837 that defines a first circle 837', and the second curvature may have second radius 838 that defines a second circle 838'. Further, in some embodiments, the first radius may be between 1.9 millimeters and 2.9 millimeters, such as 2.4 millimeters. Further still, in some embodiments, the second radius 838 may be substantially equal to the first radius 837. However, in other embodiments, the second radius 838 may be different than the first radius 837. The second radius 838 may be any of the values of the first radius 837 as described herein.

Further, the tab portion 830 of the substrate 810 may have a width dimension 839. The width dimension 839 may take the form of or be similar in form to the width dimension 439, the width dimension 339, and/or the width dimension 239. In addition, the material and/or thickness of the tab portion 830 may take the form of or be similar in form to the material and/or thickness of the tab portion 430, the tab portion 330, and/or the tab portion 230.

Moreover, the antenna 840 may include a conductive loop 842, and the conductive loop 842 may be disposed on the loop portion 820 of the substrate 810 between the inner circumference 823 and the outer circumference 821 of the loop portion 820. The antenna 840 may be configured for communications and/or harvesting energy as described herein. The conductive loop 842 may have a center diameter 844, a width dimension 846, an outer circumference 847a defined by an outer diameter, and an inner circumference 847b defined by an inner diameter.

The antenna 840 may take the form of or be similar in form to the antenna 430 and/or the antenna 330, and the conductive loop 842 may take the form of or be similar in form to the conductive loop 442 and/or the conductive loop 342. Accordingly, the center diameter 844 may take the form of or be similar in form to the center diameter 444 and/or the center diameter 344, the width dimension 846 may take the form of or be similar in form to the width dimension 446 and/or the width dimension 346, the outer circumference 847a defined by the outer diameter may take the form of or be similar in form to the outer circumference 447a defined by the outer diameter and/or the outer circumference 347a defined by the outer diameter, and the inner circumference 847b defined by the inner diameter may take the form of or be similar in form to the inner circumference 447b defined by the inner diameter and/or the inner circumference 347b defined by the inner diameter.

Further, the sensor 850 may be disposed on the tab portion 830 of the substrate 810. With this arrangement, the sensor 850 may be located inside of the conductive loop 842. The sensor 850 may be configured to detect an analyte, such as an analyte in a tear film of a user wearing an eye-mountable device. The sensor 850 may take the form of or be similar in form to the sensor 450 and/or the sensor 350.

Further still, the electronics 860 may be disposed on the tab portion 830 of the substrate 810. With this arrangement, the electronics 860 may be located inside of the conductive loop 842. The electronics 860 may include a controller 862, a capacitor 864, and a light emitting diode 866. The controller 862 may be configured to operate the sensor 850 and/or the antenna 840, the capacitor 864 may be configured to stabilize a DC voltage that is provided to the controller 862, the light emitting diode 866 may be configured to emit and/or transmit light to be perceived by an eye of a user wearing an eye-mountable device. The controller 862 may take the form of or be similar in form to the controller 462 and/or the controller 362, the capacitor 864 may take the form of or be similar in form to the capacitor 464 and/or the capacitor 364, and the light emitting diode 866 may take the form of or be similar in form to the light emitting diode 466 and/or the light emitting diode 366.

Moreover, the battery 870 may be disposed on the tab portion 830 of the substrate 810. With this arrangement, the battery 870 may be located inside of the conductive loop 842. The battery 870 may be configured to provide electrical power to the controller 862. The battery 870 may take the form of or be similar in form to the battery 470 and/or the battery 370.

The sensor 850, electronics 860, and battery 870 are disposed on the tab portion 830 of the substrate 810 in the same or similar way as the sensor 450, electronics 460, and battery 470 are disposed on the tab portion 430 of the substrate 410 and/or the sensor 350, electronics 360, and battery 470 are disposed on the tab portion 330 of the substrate 310. Moreover, the sensor 850, electronics 860, and battery 870 are connected via interconnects in the same or similar way as the sensor 450, electronics 460, and battery 470 are connected via interconnects and/or the sensor 350, electronics 360, and battery 370 are connected via the first interconnects 368a-f. Further, the sensor 850, electronics 860, and battery 870 are connected to the conductive loop 842 via interconnects in the same or similar way as the sensor 450, electronics 460, and battery 470 are connected to the conductive loop 442 via interconnects and/or the sensor 350, electronics 360, and battery 370 are connected to the conductive loop 342 via the second interconnects 369a-d.

The structure 800 may be embedded in a transparent polymer in the same or similar way as the structure 408 is embedded in the transparent polymer 402. Moreover, in some embodiments, the structure 800 may be substantially planar before being embedded in a transparent polymer. Moreover, in some embodiments, the structure 800 may be substantially planar after being embedded in an transparent polymer.

Further, in some embodiments, the structure 800 may at least partially conform to a curvature of a transparent polymer in the same or similar way as the structure 408 at least partially conforms to the curvature of the transparent polymer 402.

In some embodiments, the center diameter 844 of the conductive loop 842, the width dimension 846 of the conductive loop 842, and the width dimension 839 of the tab portion 830 of the substrate 810 may be selected based on a predetermined comfort of a wearer of the eye-mountable device 800 and/or power delivery of the antenna 840.

Moreover, in some embodiments, a conductive loop of a structure may have a cross-sectional shape oriented substantially perpendicular to an outer diameter (and/or center diameter) of the conductive loop. And in at least one such example, the cross-section shape may comprise a triangular shape. Cross-sectional shapes of the conductive loop that are oriented substantially perpendicular to the outer diameter of the conductive loop may reduce stress (e.g., radial stress and/or hoop stress) of the structure embedded in a transparent polymer.

For instance, in some embodiments, the conductive loop 342 may further include a cross-sectional shape oriented substantially perpendicular to the outer diameter of the conductive loop 340 and/or the center diameter 344 of the conductive loop 340. And in at least one such embodiment, the cross-sectional shape may comprise a triangular shape.

Moreover, in some embodiments, the conductive loop 442 may further include a cross-sectional shape oriented substantially perpendicular to the outer diameter of the conductive loop 440 and/or the center diameter 444 of the conductive loop 440. And in at least one such embodiment, the cross-sectional shape may comprise a triangular shape.

Further, in some embodiments, the conductive loop 842 may further include a cross-sectional shape oriented substantially perpendicular to the outer diameter of the conductive loop 840 and/or the center diameter 844 of the conductive loop 840. And in at least one such embodiment, the cross-sectional shape may comprise a triangular shape.

While eye-mountable devices have been described above, the structures described herein may be part of other body-mountable devices that are mounted on or in other portions of the human body.

For example, in some embodiments, structures described herein may be included in a tooth-mountable device. In some embodiments, the tooth-mountable device may take the form of or be similar in form to the eye-mountable device 110 and/or eye-mountable device 400. For instance, the tooth-mountable device could include a polymeric material and/or transparent polymer that is the same as or similar to any of the polymeric materials or transparent polymers described herein and a substrate and/or structure that is the same as or similar to any of the substrates or structures described herein. With such an arrangement, the tooth-mountable device may be configured to detect at least one analyte in a fluid (e.g., saliva) of a user wearing the tooth-mountable device.

Moreover, in some embodiments, structures described herein may be included in a skin-mountable device. In some embodiments, the skin-mountable device may take the form of or be similar in form to the eye-mountable device 110 and/or the eye-mountable device 400. For instance, the skin-mountable device could include a polymeric material and/or a transparent polymer that is the same as or similar to any of the polymeric materials or transparent polymers described herein and a substrate and/or structure that is the same as or similar to any of the substrates or structures described herein. With such an arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. An eye-mountable device comprising:
   a transparent polymer, wherein the transparent polymer defines a posterior side and an anterior side of the eye-mountable device; and a structure embedded in the transparent polymer, wherein the structure comprises:
- a substrate comprising a loop portion and a tab portion, wherein the loop portion has an outer edge and an inner edge, wherein the tab portion extends from the loop portion towards an area encircled by the loop portion, and wherein the tab portion defines a bend in the inner edge,
- an antenna comprising a conductive loop, wherein the conductive loop is disposed on the loop portion of the substrate between the inner edge and the outer edge, and
- a sensor disposed on the tab portion of the substrate.

2. The eye-mountable device of claim 1, wherein the tab portion of the substrate has an inner edge and first and second side edges that extend inwardly from the loop portion of the substrate to the inner edge of the tab portion of the substrate.

3. The eye-mountable device of claim 2, wherein the first and second side edges of the tab portion of the substrate are substantially perpendicular to the inner edge of the loop portion of the substrate.

4. The eye-mountable device of claim 2, wherein the tab portion of the substrate has a width dimension between about 1 millimeter and about 2 millimeters.

5. The eye-mountable device of claim 1, wherein the conductive loop has a width dimension between 250 micrometers and 350 micrometers.

6. The eye-mountable device of claim 1, wherein the conductive loop comprises a metal layer coated with a barrier layer.

7. The eye-mountable device of claim 6, wherein the barrier layer extends from the metal layer a distance between 25 micrometers and 125 micrometers.

8. The eye-mountable device of claim 6, wherein the barrier layer has a thickness less than 5 nanometers.

9. The eye-mountable device of claim 1, wherein the structure further comprises one or more electronic components disposed on the tab portion of the substrate, wherein the one or more electronic components are configured to operate the sensor and the antenna.

10. The eye-mountable device of claim 9, wherein the one or more electronic components include an integrated circuit and a capacitor, wherein the integrated circuit and capacitor are spaced apart a distance between 0.9 millimeters and 1.3 millimeters.

11. The eye-mountable device of claim 9, wherein the structure further comprises a battery disposed on the tab portion of the substrate.

12. The eye-mountable device of claim 9, wherein the one or more electronic components disposed on the tab portion are coated with a barrier layer.

13. The eye-mountable device of claim 1, wherein the sensor is at least partially coated with a barrier layer.

14. The eye-mountable device of claim 1, wherein the structure is substantially planar.

15. The eye-mountable device of claim 1, wherein the transparent polymer has a curvature, and the structure at least partially conforms to the curvature of the transparent polymer.

16. The eye-mountable device of claim 1, wherein the tab portion of the substrate has an inner edge, and wherein the inner edge of the tab portion of the substrate has first and second ends that contact the inner edge of the loop portion of the substrate.

17. The eye-mountable device of claim 16, wherein the first end of the inner edge of the tab portion of the substrate has a first curvature, and wherein the second end of the inner edge of the tab portion of the substrate has a second curvature.

18. The eye-mountable device of claim 17, wherein the first curvature is between about 1.9 millimeters and 2.9 millimeters.

19. A structure configured to be embedded in a transparent polymer, the structure comprising:
- a substrate comprising a loop portion and a tab portion, wherein the loop portion has an outer edge and an inner edge, wherein the tab portion extends from the loop portion towards an area encircled by the loop portion, and wherein the tab portion defines a bend in the inner edge;
- an antenna comprising a conductive loop, wherein the conductive loop is disposed on the loop portion of the substrate between the inner edge and the outer edge; and
- a sensor disposed on the tab portion of the substrate, wherein the transparent polymer defines a posterior side and an anterior side of an eye-mountable device.

20. The structure of claim 19, wherein the tab portion comprises an inner edge and first and second side edges that extend inwardly from the loop portion of the substrate to the inner edge of the tab portion of the substrate.

* * * * *